(12) United States Patent
Woolfson et al.

(10) Patent No.: US 11,821,903 B2
(45) Date of Patent: Nov. 21, 2023

(54) SENSOR

(71) Applicant: The University of Bristol, Bristol (GB)

(72) Inventors: Derek Neil Woolfson, Bristol (GB); William Michael Dawson, Bristol (GB); Guto Glyn Rhys, Bristol (GB); David Arne Scott, Bristol (GB); Jordan Michael Fletcher, Bristol (GB); Christopher Robin Wells Wood, Bristol (GB)

(73) Assignee: The University of Bristol, Bristol (GB)

( * ) Notice: Subject to any disclaimer, the term of this patent is extended or adjusted under 35 U.S.C. 154(b) by 692 days.

(21) Appl. No.: 16/644,926

(22) PCT Filed: Sep. 6, 2018

(86) PCT No.: PCT/GB2018/052521
§ 371 (c)(1),
(2) Date: Mar. 5, 2020

(87) PCT Pub. No.: WO2019/048859
PCT Pub. Date: Mar. 14, 2019

(65) Prior Publication Data
US 2021/0072253 A1    Mar. 11, 2021

(30) Foreign Application Priority Data

Sep. 8, 2017 (GB) .................................. 1714478

(51) Int. Cl.
*G01N 33/68* (2006.01)
*G01N 21/64* (2006.01)
*G01N 33/53* (2006.01)

(52) U.S. Cl.
CPC ..... *G01N 33/6845* (2013.01); *G01N 21/6428* (2013.01); *G01N 33/5308* (2013.01)

(58) Field of Classification Search
CPC ........... G01N 33/6845; G01N 21/6428; G01N 33/5308; G01N 33/68; C07K 7/06
See application file for complete search history.

(56) References Cited

U.S. PATENT DOCUMENTS

| 6,503,511 | B1 * | 1/2003 | Wizemann | ......... | C07K 14/3156 |
| | | | | | 424/234.1 |
| 7,622,295 | B2 * | 11/2009 | Cabezas | ................... | G01N 1/06 |
| | | | | | 435/287.2 |

(Continued)

FOREIGN PATENT DOCUMENTS

| WO | WO97/41424 A | 11/1997 |
| WO | WO2013/121201 A | 8/2013 |
| WO | WO2015/120548 A | 8/2015 |

OTHER PUBLICATIONS

De la Rica (Adv. Func Mater. 2011 21:1018-1026). (Year: 2011).*

(Continued)

*Primary Examiner* — Changhwa J Cheu
(74) *Attorney, Agent, or Firm* — Stites & Harbison PLLC; Mandy Wilson Decker

(57) ABSTRACT

A sensor array comprising at least two sensors, wherein each sensor comprises a protein barrel and a reporter dye; wherein the protein barrel defines a lumen; the reporter dye is bound to the lumen reversibly; and wherein the protein barrel is different in structure in the at least two sensors.

18 Claims, 10 Drawing Sheets

Specification includes a Sequence Listing.

(56) References Cited

U.S. PATENT DOCUMENTS

2006/0009620 A1* 1/2006 Woolfson .............. G01Q 70/12
530/350
2010/0075434 A1 3/2010 Tamamura et al.

OTHER PUBLICATIONS

Raliski (Bioconjugate Chem. 2014 25:1916-1920). (Year: 2014).*
Tinberg, et al: "Computational design of ligand-binding proteins with high affinity and selectivity", Nature, vol. 501, No. 7466, Sep. 4, 2013 (Sep. 4, 2013), pp. 212-216.
Polizzi et al: "De nova design of a hyperstable non-natural protein-ligand complex with sub-A accuracy", Nature Chemistry, vol. 9, No. 12, Aug. 21, 2017 (Aug. 21, 2017), pp. 1157-1164.
Pastukhov Alexander V et al: Fluorescent dyes as probes to study lipid-binding proteins, Proteins, vol. 53, No. 3, Nov. 15, 2003 (Nov. 15, 2003), pp. 607-615.
Ory et al: "Studies of the Ligand Binding Reaction of Adipocyte Lipid Binding Protein Using the Fluorescent Probe 1,8-Anilinonaphthalene-8-Sulfonate", Biophysical Journal, vol. 77, No. 2, Aug. 1, 1999 (Aug. 1, 1999), pp. 1107-1116.
Thomson:, A. Computational design of water soluble alpha-helical barrels, Science, vol. 346, No. 6208, Oct. 23, 2014 (Oct. 23, 2014), p. 485.
Burgess et al., "Modular Design of Self-Assembling Peptide-Based Nanotubes", J American Chemical Society, vol. 137, 2015, NC 10554-10562.
Umali & EV Anslyn, "A general approach to differential sensing using synthetic molecular reporters", Curr Opin Chem Biol, vol. 14, 2010, AP 685-692.
Hina National Intellectual Property Administration, Notification of the First Office Action issued in rresponding Application No. 201880058404.2, dated Mar. 1, 2023.
Zaccai, et al., A de novo peptide hexamer with a mutable channel, nature CHeMICaL Biology | vol. 7 | Dec. 2011, pp. 935-941.
Huang, et al., High thermodynamic stability of parametrically designed helical bundles; Science; Oct. 24, 2014; vol. 346; Issue 6208; pp. 481-484.
Thomson, et al., Computational design of water-soluble a-helical barrels; Science; Oct. 24, 2014; vol. 346; Issue 6208; pp. 485-488.
Woolfson, Derek N., The Design of Coiled-Coil Structures and Assemblies; Advances in Protein Chemistry, 2005, vol. 7, pp. 79-112.
Woolfson, Derek N., Chapter 2 Coiled-Coil Design: Updated and Upgraded, Fibrous Proteins: Structures and Mechanisms, Subcellular Biochemistry 82, 2017, pp. 35-61.

* cited by examiner

SEQUENCE LISTING

```
<160> NUMBER OF SEQ ID NOS: 48

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1

Leu Gln Lys Ile Glu Xaa Ile
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Leu Lys Ala Ile Ala Xaa Glu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid
```

-continued

```
<400> SEQUENCE: 3

Leu Lys Glu Ile Ala Xaa Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 4

Ile Lys Glu Ile Ala Xaa Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 5

Leu Lys Glu Ile Ala Xaa Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(6)
<223> OTHER INFORMATION: Xaa can be any naturally occuring amino acid

<400> SEQUENCE: 6

Phe Lys Glu Ile Ala Xaa Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 7

Ile Lys Glu Ile Ala Xaa Ala
1               5

<210> SEQ ID NO 8
<211> LENGTH: 7
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 8

Ile Lys Glu Val Ala Xaa Ala
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 9

Val Lys Glu Val Ala Xaa Ala
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 10

Val Lys Glu Ile Ala Xaa Ala
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 11

Met Lys Glu Ile Ala Xaa Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 12

Leu Lys Gln Ile Glu Xaa Ile
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 13

Leu Lys Glu Val Ala Xaa Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 14

Val Lys Glu Leu Ala Xaa Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 15

Ile Lys Glu Leu Ser Xaa Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 16

Ile Lys Glu Leu Ala Xaa Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid
```

<400> SEQUENCE: 17

Leu Lys Glu Leu Ala Xaa Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 18

Phe Lys Glu Ile Ala Xaa Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 19

Leu Lys Glu Leu Ala Xaa Ala
1               5

<210> SEQ ID NO 20
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 20

Gly Lys Ile Glu Gln Ile Leu Gln Lys Ile Glu Lys Ile Leu Gln Lys
1               5                   10                  15

Ile Glu Trp Ile Leu Gln Lys Ile Glu Gln Ile Leu Gln Gly
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 21

Gly Glu Leu Lys Ala Ile Ala Gln Glu Leu Lys Ala Ile Ala Lys Glu
1               5                   10                  15

Leu Lys Ala Ile Ala Trp Glu Leu Lys Ala Ile Ala Gln Gly
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic Peptide

```
<400> SEQUENCE: 22

Gly Glu Ile Ala Lys Ser Leu Lys Glu Ile Ala Lys Ser Leu Lys Glu
1               5                   10                  15

Ile Ala Trp Ser Leu Lys Glu Ile Ala Lys Ser Leu Lys Gly
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 23

Gly Glu Ile Ala Gln Ala Leu Arg Glu Ile Ala Lys Ala Leu Arg Glu
1               5                   10                  15

Ile Ala Trp Ala Leu Arg Glu Ile Ala Gln Ala Leu Arg Gly
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 24

Gly Glu Ile Ala Lys Ser Leu Lys Glu Lys Ala Lys Ser Leu Lys Glu
1               5                   10                  15

Ile Ala Trp Ser Leu Lys Glu Ile Ala Lys Ser Leu Lys Gly
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 25

Gly Glu Ile Ala Gln Ala Leu Arg Glu Ile Ala Lys Ala Leu Arg Glu
1               5                   10                  15

Lys Ala Trp Ala Leu Arg Glu Ile Ala Gln Ala Leu Arg Gly
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 26

Gly Glu Ile Ala Lys Ala Leu Arg Glu Ile Ala Lys Ala Leu Arg Glu
1               5                   10                  15

Ile Ala Trp Ala Leu Arg Glu Asp Ala Lys Ala Leu Arg Gly
            20                  25                  30

<210> SEQ ID NO 27
<211> LENGTH: 30
<212> TYPE: PRT
<213> ORGANISM: Artificial Sequence
<220> FEATURE:
```

<223> OTHER INFORMATION: Synthetic Peptide

<400> SEQUENCE: 27

Gly Glu Ile Ala Gln Ala Leu Arg Glu Ile Ala Lys Ala Leu Arg Glu
1               5                   10                  15

Ile Ala Trp Ala Leu Arg Glu Lys Ala Gln Ala Leu Arg Gly
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 28

Gly Glu Ile Ala Lys Ala Leu Arg Glu Ile Ala Lys Ala Leu Arg Glu
1               5                   10                  15

Ile Ala Trp Ala Leu Arg Glu Glu Ala Lys Ala Leu Arg Gly
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 29

Gly Glu Val Ala Gln Ala Ile Lys Glu Val Ala Lys Ala Ile Lys Glu
1               5                   10                  15

Val Ala Trp Ala Ile Lys Glu Val Ala Gln Ala Ile Lys Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 30

Gly Glu Ile Ala Gln Ala Ile Lys Glu Ile Ala Lys Ala Ile Lys Glu
1               5                   10                  15

Ile Ala Trp Ala Ile Lys Glu Ile Ala Gln Ala Ile Lys Gly
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 31

Gly Glu Ile Ala Gln Ala Val Lys Glu Ile Ala Lys Ala Val Lys Glu
1               5                   10                  15

Ile Ala Trp Ala Val Lys Glu Ile Ala Gln Ala Val Lys Gly
            20                  25                  30

<210> SEQ ID NO 32
<211> LENGTH: 30
<212> TYPE: PRT
<213> ORGANISM: Artificial Sequence

```
<220> FEATURE:
<223> OTHER INFORMATION: Synthetic Peptide

<400> SEQUENCE: 32

Gly Glu Val Ala Gln Ala Val Lys Glu Val Ala Lys Ala Val Lys Glu
1               5                   10                  15

Val Ala Trp Ala Val Lys Glu Val Ala Gln Ala Val Lys Gly
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 33

Gly Glu Val Ala Gln Ala Leu Lys Glu Val Ala Lys Ala Leu Lys Glu
1               5                   10                  15

Val Ala Trp Ala Leu Lys Glu Val Ala Gln Ala Leu Lys Gly
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 34

Gly Glu Leu Ala Gln Ala Val Lys Glu Leu Ala Lys Ala Val Lys Glu
1               5                   10                  15

Leu Ala Trp Ala Val Lys Glu Leu Ala Gln Ala Val Lys Gly
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 35

Gly Glu Leu Ala Gln Ser Ile Lys Glu Leu Ala Lys Ser Ile Lys Glu
1               5                   10                  15

Leu Ala Trp Ser Ile Lys Glu Leu Ala Gln Ser Ile Lys Gly
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 36

Gly Glu Leu Ser Gln Ala Ile Lys Glu Leu Ser Lys Ala Ile Lys Glu
1               5                   10                  15

Leu Ser Trp Ala Ile Lys Glu Leu Ser Gln Ala Ile Lys Gly
            20                  25                  30

<210> SEQ ID NO 37
<211> LENGTH: 30
<212> TYPE: PRT
```

<213> ORGANISM: Artificial Sequence
<220> FEATURE:
<223> OTHER INFORMATION: Synthetic Peptide

<400> SEQUENCE: 37

Gly Glu Leu Ala Gln Ser Ile Lys Glu Leu Ala Lys Ser Ile Lys Glu
1               5                   10                  15
Glu Ala Trp Ser Ile Lys Glu Leu Ala Gln Ser Ile Lys Gly
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 38

Gly Glu Leu Ala Gln Ala Leu Lys Glu Leu Ala Lys Ala Leu Lys Glu
1               5                   10                  15
Leu Ala Trp Ala Leu Lys Glu Leu Ala Gln Ala Leu Lys Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Artificial Peptide

<400> SEQUENCE: 39

Gly Glu Leu Ala Gln Ser Leu Lys Glu Leu Ala Lys Ser Leu Lys Glu
1               5                   10                  15
Leu Ala Trp Ser Leu Lys Glu Leu Ala Gln Ser Leu Lys Gly
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Artificial Peptide

<400> SEQUENCE: 40

Gly Glu Leu Ala Gln Ala Leu Lys Glu Leu Ala Lys Ala Leu Lys Glu
1               5                   10                  15
Gln Ala Trp Ala Leu Lys Glu Leu Ala Gln Ala Leu Lys Gly
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Artificial Peptide

<400> SEQUENCE: 41

Gly Glu Leu Ala Gln Ala Leu Lys Glu Leu Ala Lys Ala Leu Lys Glu
1               5                   10                  15
Glu Ala Trp Ala Leu Lys Glu Leu Ala Gln Ala Leu Lys Gly
            20                  25                  30

<210> SEQ ID NO 42
<211> LENGTH: 30

```
<212> TYPE: PRT
<213> ORGANISM: Artificial Sequence
<220> FEATURE:
<223> OTHER INFORMATION: Artificial Peptide

<400> SEQUENCE: 42

Gly Glu Ile Ala Gln Ala Phe Lys Glu Ile Ala Lys Ala Phe Lys Glu
1               5                   10                  15

Ile Ala Trp Ala Phe Lys Glu Ile Ala Gln Ala Phe Lys Gly
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Artificial Peptide

<400> SEQUENCE: 43

Gly Glu Ile Ala Gln Ala Met Lys Glu Ile Ala Lys Ala Met Lys Glu
1               5                   10                  15

Ile Ala Trp Ala Met Lys Glu Ile Ala Gln Ala Met Lys Gly
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Artificial Peptide

<400> SEQUENCE: 44

Gly Glu Ile Ala Gln Ala Leu Lys Glu Ile Ala Lys Ala Leu Lys Glu
1               5                   10                  15

Cys Ala Trp Ala Leu Lys Glu Ile Ala Gln Ala Leu Lys Gly
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(29)
<223> OTHER INFORMATION: D-amino acid residue

<400> SEQUENCE: 45

Gly Glu Val Ala Gln Ala Val Lys Glu Val Ala Lys Ala Val Lys Glu
1               5                   10                  15

Val Ala Trp Ala Val Lys Glu Val Ala Gln Ala Lys Val Gly
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (24)..(24)
<223> OTHER INFORMATION: Nle

<400> SEQUENCE: 46
```

```
<210> SEQ ID NO 47
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (28)..(28)
<223> OTHER INFORMATION: Nle

<400> SEQUENCE: 47

Gly Glu Ile Ala Gln Ala Leu Arg Glu Ile Ala Lys Ala Leu Arg Glu
1               5                  10                  15

Ile Ala Trp Ala Leu Arg Glu Ile Ala Gln Ala Leu Arg Gly
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: dehydroleucine
<220> FEATURE:
<221> NAME/KEY: MISC_FEATURE
<222> LOCATION: (14)..(14)
<223> OTHER INFORMATION: dehydroleucine
<220> FEATURE:
<221> NAME/KEY: MISC_FEATURE
<222> LOCATION: (21)..(21)
<223> OTHER INFORMATION: dehydroleucine
<220> FEATURE:
<221> NAME/KEY: MISC_FEATURE
<222> LOCATION: (28)..(28)
<223> OTHER INFORMATION: dehydroleucine

<400> SEQUENCE: 48

Gly Glu Ile Ala Gln Ala Leu Arg Glu Ile Ala Lys Ala Leu Arg Glu
1               5                  10                  15

Ile Ala Trp Ala Leu Arg Glu Ile Ala Gln Ala Leu Arg Gly
            20                  25                  30
```

SENSOR

CROSS REFERENCE TO RELATED APPLICATIONS

This application is a § 371 National State Application of PCT/GB2018/052521 filed Sep. 6, 2018 which claims priority to GB 1714478.3 filed Sep. 8, 2017.

SEQUENCE LISTING

The instant application contains a Sequence Listing which has been submitted in ASCII format via EFS-Web and is hereby incorporated by reference in its entirety. The ASCII copy of the Sequence Listing, which was created on Nov. 14, 2018, is named P123129PCT_Sequence listing.txt, and is 16.2 kilobytes in size.

FIELD OF INVENTION

The present invention relates to sensor arrays that work by displacement of reporter dyes from protein barrels. Specifically, the invention relates to sensor arrays that are analysed by differential methods, often referred to as "artificial olfaction" or "artificial nose" methods.

BACKGROUND TO THE INVENTION

There are two main approaches to sensing using biomolecules or bio-inspired molecules. The first is a "lock-and-key" approach, where a highly specific sensor molecule such as an antibody is produced for each analyte of interest. These types of sensor must be optimised to be highly selective for the target analyte, and therefore need to go through an expensive development and optimisation processes for each analyte.

A second approach is analogous to olfactory systems and uses an array of less-specific receptors. The concept is that a single target molecule or mixture binds and/or reacts with several of these receptors to different extents giving a unique signature in the array. This circumvents the need to develop the highly specific and often expensive receptors for each analyte. This second approach is referred to as differential or array sensing.

A first approach to differential sensing is where an array of dye molecules are designed and the analyte directly binds to, or chemically reacts with, the dye molecules. You, Zha and Anslyn (2015) provides a comprehensive review of such arrays and their applications. However, such arrays are complex to design because bespoke dyes must typically be designed, and these dyes must (a) provide an optical signal, (b) bind a variety of analytes, and (c) change in optical properties upon binding. Even once discovered, these bespoke dyes can involve complicated syntheses and expensive materials, increasing the cost of the final arrays.

A different approach to differential sensing is to use displacement of a reporter dye from a receptor. This allows the diversity to be engineered into the receptor rather than the dye, which enables the use of low-cost routine dyes as reporter dyes. A review of such arrays can also be found in You, Zha and Anslyn (2015). Specific representative examples are discussed below.

A commonly used receptor/dye combination is an ensemble of a short peptide, metal ion and reporter dye. The metal ion binds to both the short peptide and the reporter dye, and the analyte displaces the reporter dye from the metal ion. Umali and Anslyn (2010) describe a number of variations to this ensemble that can be used for different analyte classes. For example, in one array the peptides were decorated with guanidinium groups for binding nucleotide phosphates, and in another array the peptides were decorated with boronic acid groups for binding glycopeptides and saccharides. In more recent work, such arrays were used to characterise polyphenol compositions of wines (Umali et al., 2015) and cachaça wood extracts (Ghanem et al., 2017). These ensemble sensing arrays, however, require the careful preparation of the ensembles from at least three components, the reporter dye, the metal ion and at least one peptide. Due to the requirement for reporter dyes that bind to metal ions, and analytes that can displace the reporter dyes from binding with metal ions, such arrays also lack sensitivity towards non-polar, hydrophobic molecules.

An approach that avoids the need for a metal ion has been to use serum albumins as the receptor. Serum albumins from different source animals has been used to provide a variety of receptors, and a variety of hydrophobic dyes were used to bind within the serum albumin binding sites. These arrays have been used to discriminate between terpenes (Adams and Anslyn, 2009), fatty acids and oils (Kubarych, 2010), glycerides (Diehl et al., 2015) and the plasticisers found in different plastic explosives (Ivy et al., 2012). While useful, arrays based on serum albumins are limited to the detection and discrimination of hydrophobic molecules such as those discussed above.

The present invention seeks to provide a simple, low-cost and robust receptor and dye system that can form arrays for detecting and distinguishing between analytes from a very broad spectrum of analyte classes. As such, the present invention seeks to overcome the limitations of the prior art.

SUMMARY OF THE INVENTION

According to a first aspect the invention provides a sensor array comprising at least two sensors, wherein each sensor comprises a protein barrel and a reporter dye; wherein the protein barrel defines a lumen; the reporter dye is bound to the lumen reversibly; and wherein the protein barrel is different in structure in the at least two sensors.

The reporter dye is a dye that provides a different optical signal between being bound to the lumen in the absence of any analyte and when this binding is disrupted. Disruption includes the reporter dye being ejected from the lumen or the reporter dye changing in configuration within the lumen. In the absence of an analyte, the reporter dye is bound to the lumen and produces a first optical signal. In the presence of an analyte, the reporter dye is either displaced entirely from the lumen or remains within the lumen in a different configuration, such that the signal of the reporter dye is changed.

Any individual sensor typically comprises multiple protein barrels. An analyte that results in ejection of the reporter dye from the lumen will not typically result in ejection of dye from all protein barrels within a sensor. Such an analyte will modify the dissociation constant of the reporter dye, either by direct competition with the dye or through allosteric effects, so that the equilibrium position of binding versus not binding of the reporter dye is shifted.

By using protein barrels with different structures in the different sensors, an analyte will interact with the different protein barrel structures to different extents, affecting the optical properties of the sensor to different extents, and generating an optical signal pattern across the sensor array that is specific to that analyte.

The use of protein barrels, such as alpha helical barrels, beta barrels or ion channels, in displacement-based differential sensing provides a number of advantages over prior art techniques. For instance, in contrast to prior art techniques, protein barrels are not limited to detection of specific analyte classes and offer the ability to successfully distinguish a vast spectrum of target molecules and mixtures, including both hydrophobic and non-hydrophobic analytes.

One reason for this is that the structure of the protein barrel provides for a very large surface area on the lumen surface. The bound reporter dye is surrounded on all sides by the lumen surface, meaning that the chemical environment of the reporter dye is directly dictated by the large number of amino acid side chains of the lumen surface. In more detail, for an alpha helical barrel it is common that there are up to 8 amino acid side chains per helix that form the lumen surface, i.e. 40 amino acid side chains for an alpha helical barrel with five helices, 48 amino acid side chains for an alpha helical barrel with six helices and so on. This large surface area is advantageously provided on a rigid protein barrel where any or in theory all amino acid side chains on the lumen surface can be modified to ultimately provide a massive variety of different protein barrels with different chemical environments. In one embodiment up to 50% of the amino acid side chains are modified, for example 4 per chain in the lumen surface of the heptamer, so 28 in total.

Even when limiting to the 20 ribosomal, standard or proteinogenic amino acids being possible at each residue, this already provides for a massive variety in chemical environment. Therefore, the different barrels used in the sensor array may be selected from multiple millions of possible options, allowing use of protein barrels with very diverse properties. Attempting to access such variety using a protein such as serum albumin would most likely result in disruption of the tertiary structure, leading to precipitated protein with complete loss of binding ability.

Surprisingly, protein barrel sensors are not limited to analytes that can bind within the protein barrel lumen. Analyte interactions with the exterior of the protein barrel can therefore modify the environment within the protein barrel lumen, in a manner analogous to allosteric modulation of receptor binding sites found in nature. This modification can change the binding constant of the reporter dye, expelling a proportion or all of the reporter dye, or this modification can change the lumen such that the reporter dye remains bound but with different optical properties. Irrespective of the underlying reason, this effect affords the ability for the sensor array to be used on a broader spectrum of analytes than just those that can bind within the lumen. The large external surface area is again provided on a rigid protein barrel where any or all amino acid side chains on the external surface can be modified to provide a massive variety of chemical environments Furthermore, for each sensor the observed signal is not a simple binary signal, such as "fluorescent" or "not fluorescent". Instead, there is a continuum between full signal and no signal. With such a massive chemical space of possible protein barrels, and with each specific protein barrel within that chemical space providing for a continuum response, the sensor assay of the invention offers access to a previously unattainable analysis space. The overall effect of this is a sensor array with an unrivalled ability to distinguish amongst a broad spectrum of analytes.

We have already noted a significant advantage of a very stable tertiary structure is that the structure can readily accommodate point mutations, particularly of residues whose side chains are directed internally within the lumen or externally toward bulk solvent.

This means that the massive chemical space referred to above can feasibly be accessed without compromising the protein barrel fold. This stability of the protein barrel tertiary structure further means that it is straightforward to computationally model the structures and use rational design concepts to create an array with the desired diversity.

Another advantage of the stable and well-defined tertiary structure of a protein barrel is high reproducibility across repeat assays. The stability of protein barrels means that they remain stable over long periods of time, affording a long shelf life and/or repeated use of the sensor array, and produce the same reliable signal in response to the same analytes. Furthermore, the barrels can be freeze dried, which allows better, safer and longer storage. The barrels are then reconstituted just by adding aqueous buffer.

Protein barrels can also be produced at very low cost, either through established peptide synthesis techniques or through recombinant expression of synthetic genes. This low cost enables mass production and/or disposable sensor arrays.

The sensor array can therefore be deployed for a wide variety of applications. For example, the sensor array can be used to identify specific compounds within complex mixtures, to differentiate between complex mixtures or to differentiate between very similar molecules, including enantiomers and enantiomeric mixtures. Specific examples discussed herein encompass the detection of a variety of both small molecules and biomolecules such as proteins. A wide range of applications are envisioned, such as detecting water contamination, food spoilage, toxins, explosives, molecules of interest in fine-chemical and pharmaceutical production processes, infection and biomarkers for disease.

In the food and drink industry it would be desirable to use the sensor array as an artificial nose, to detect gaseous compounds in the headspace above food or drink that could be indicative of spoilage. This is a possibility in the present invention, particularly when using a hydrogel substrate.

The reporter dye of the sensor array provides an optical signature, allowing for development of a sensitive but low-cost disposable chip that could be read and processed using a portable handheld device or a smartphone. In the long term, the portability of the device will facilitate 'in line', 'in field', or 'at bedside' analysis; in other words, bringing analysis to the problem not the problem to the lab. In particular, this technology allows for powerful yet cheap sensor devices that could be used in third-world or humanitarian applications such as rapid testing for quality of water, food-borne toxins, infectious disease, and so on.

As discussed above, the protein barrel may be an alpha helical barrel, beta-barrel or ion channel. When the protein barrel is an alpha helical barrel, the protein barrel comprises five or more alpha helices arranged as the alpha helical barrel.

Alpha helical barrels are particularly preferred as the protein barrel. Alpha helical barrels are typically water soluble with a hydrophobic lumen. Both natural and de novo designed alpha helical barrels are known, see Malashkevich et al., 1996; Koronakis et al., 2000; Zaccai et al., 2011; Fletcher, 2012; Meusch et al., 2014; Sun et al., 2014; Thomson et al., 2014; Collie, 2015; and Lombardo et al., 2016. Alpha helical barrels comprise coiled-coil oligomers where the defining feature is the presence of a lumen. While coiled-coil oligomers with fewer than five alpha helices are known, five alpha helices appears to be the minimum number required to define a lumen. Alpha helical barrels with five, six, seven, eight, ten and twelve alpha helices have been reported.

The size of alpha helical barrels can be very precisely controlled. Controlling the lengths of the constituent alpha helices can control the length of alpha helical barrels. Varying the number of alpha helices that make up the alpha helical barrel can control the diameter of the lumen.

Alpha helical barrels have a very stable tertiary (3D) structure. Furthermore, alpha helices comprise a very predictable heptad repeat sequence. This allows for accurate modelling of the amino acid residues that form and stabilise the alpha helical barrel tertiary (3D) structure and the amino acid residues on the lumen surface and external surface of the alpha helical barrel (as reported, for example, in Thomson et al., 2014). The stability of alpha helical barrels also allows for the sensor array to be dried and reconstituted, washed in non-aqueous solvents and/or immobilised on a solid support.

Alpha helical barrels are synthetically accessible. Alpha helical barrels can comprise identical alpha helices, wherein each alpha helix comprises an identical but separate amino acid chain. This means that only a single alpha helix needs to be synthesised, after which the alpha helical barrel will self-assemble. This simplifies and lowers the cost of synthesising alpha helical barrels.

The alpha helices typically comprise a sequence having a repeat unit with sequence abcdefg, wherein 50% or more of the a and d positions are hydrophobic amino acids and wherein 50% or more of the b, c, e, f and g positions are polar amino acids.

The nature of the alpha helical heptad repeat unit typically means that the a and d positions form the lumen surface, i.e. the internal surface of the alpha helical barrel that defines the lumen.

An important feature of alpha helical barrels is that the rigid nature of the tertiary (3D) structure allows for multiple amino acid residues to be varied simultaneously. The lumen of an alpha helical barrel is typically hydrophobic. However, up to 50% of the amino acid side chains facing into the lumen can be changed for any other amino acid. Even very polar or charged functional groups may be used. Due to the rigid nature of the alpha helical barrel, the barrel can be designed so that polar functional groups can be very precisely positioned in the otherwise hydrophobic lumen without causing unfolding of the alpha helical barrel.

With a hydrophobic lumen, the reporter dye typically should be hydrophobic. However, with polar residues in the lumen, a wider variety of dyes can be accommodated. For analytes that bind within the lumen, a similar variety of analytes can be accommodated. However, as discussed above, the analyte may also interact with the external surface of the alpha helical barrel.

In specific embodiments the repeat unit can be selected from the list consisting of: LQKIEfI LKAIAfE, LKEIAfS, IKEIAfS, LKEIAfA, FKEIAfA, IKEIAfA, IKEVAfA, VKEVAfA, VKEIAfA, MKEIAfA, LKQIEfI, LKEVAfA, VKELAfA, IKELSfA, IKELAfS, LKELAfS, FKEIAfA and LKELAfA; wherein f may vary between repeat units. These repeat sequences reflect repeat units of de novo alpha helical barrels that form five-, six-, seven and eight-membered alpha helical barrels. While these repeat units represent the basic building block of an alpha helix, there may of course be point mutations such that not every unit is an identical repeat. In any given alpha helix, or in the alpha helical barrel, up to 40%, preferably up to 25%, more preferably up to 10%, of the amino acid residues may deviate from the repeat unit.

In a heptad repeat unit where the a and d positions form the hydrophobic core, the f position typically represents an amino acid where the side chain points directly into the bulk solvent. As such, the amino acid at the f position can vary between repeat units.

Each alpha helix can comprise at least three repeat units. Three repeat units provides for a lumen of sufficient length to bind a wide range of reporter dyes.

The entire protein barrel may comprise ribosomal, standard or proteinogenic amino acid enantiomers. Alternatively, the protein barrel can comprise a non-natural amino acid. A fully enantiomeric protein barrel can form the basis for detection of enantiomeric analytes. Artificial amino acids can also be incorporated. Artificial amino acids can include natural amino acids that have been further functionalised. In one particular embodiment, the natural amino acids may have been further functionalised by post-translational modification, such as by phosphorylation or glycosylation.

The non-natural amino acid can be an amino acid that has been modified by chemically linking a protein substrate. Specifically, the protein substrate can comprise an enzyme substrate, receptor substrate and/or antibody substrate. The protein substrate may simply be for the protein binding site to bind to. The protein substrate may also be a reaction site that an enzyme can modify. For example, the protein substrate may be a phosphorylation substrate for a kinase. As such, the reporter dye signal may be affected upon binding by the kinase, or by phosphorylation.

The protein barrel can comprise a single and continuous amino acid backbone. As such, the protein does not self-assemble from separate protein subunits. As such, the manner of self-assembly from protein subunits (i.e. quaternary structure) does not need to be considered. A single and continuous amino acid backbone can therefore further constrain where elements of the protein secondary structure become located in the fold.

With alpha helical barrels, for example, each helix may have a different structure, or just one helix of the barrel may contain a charged residue. With separate alpha helix subunits, consideration would need to be given to the different permutations of helical barrels that could form. With a single and continuous amino acid backbone, this consideration can be largely removed by careful design of a single and continuous amino acid backbone that folds into the alpha helices (i.e. the secondary structure) that in turn folds into the alpha helix barrel (i.e. the tertiary structure).

Overall, significant control over making specific changes to a protein barrel structure can be gained.

The protein barrel can be in solution, but in one embodiment of the invention the protein barrel is immobilised on a substrate. This allows for sensor arrays where analyte solutions can flow over the sensors, or where sensors can be washed and used again. Furthermore, immobilisation provides for sensor arrays where there are no physical barriers between sensors, providing the basis for array microchips. The amounts of protein barrel needed for such array microchips would be miniscule, probably less than one microgram, such as 0.01 to 1 microgram.

The reporter dye can also be immobilised on the substrate, or on the protein barrel, as long as the reporter dye is still able to reversibly access the protein barrel lumen. Such immobilisation provides for protein barrels and reporter dyes that cannot wash away or interfere with neighbouring sensors, and provides for reusable sensor arrays or sensor arrays that can be used for in-line sensing.

The protein barrel can also be situated on or in a hydrogel, or 3-dimensional porous scaffolds. This helps to allow the barrel to be used for sensing gaseous analytes which can dissolve in the hydrogel and become accessible to the barrel.

The protein barrel and reporter dye can be in a dry state. In other words, the complex of the protein barrel and reporter dye has been dried. The sensor array is therefore in a dry state. The dry state is suitable for storage, but would typically be rehydrated before carrying out analysis. If the analyte is aqueous, rehydration could be achieved in a simple manner by the analyte. The use of a dry state is made possible by the protein barrels being highly stable.

In a preferred embodiment, the reporter dye provides an optical signal when bound to the lumen. By this, we mean that there is a measurable optical signal when the reporter dye is bound to the lumen. Typically, this would mean that there is no optical signal when the reporter dye is in free solution. This has advantages over the inverse scenario, where the reporter dye provides a signal in free solution but provides no signal when bound to the lumen, but the inverse scenario is also possible.

The resting state of the reporter being bound to the protein barrel, before any analyte is added, is a state where a positive signal can be measured. This provides a quick way of checking that the reporter dye and protein barrel in each sensor are intact before starting the assay. In addition, it is postulated that in certain cases the reporter dye may not leave the lumen in response to an analyte. The reporter dye instead adopts a different configuration within the lumen, possibly in response to a change in the lumen configuration, this change in configuration also causing a change in optical properties. If the reporter dye was quenched on being bound, such changes would not be observable. This furthermore allows for a reporter dye to be encapsulated within the lumen, perhaps by appending blocking groups on either end of the lumen after the reporter dye is bound. Such a complex would operate by changes in configuration of the reporter dye within the lumen in response to target analytes. Encapsulating reporter dyes in this way allows for robust sensors that can be reused, or used in applications such as in line sensors, as the reporter dye would not wash away.

The reporter dye can be a compound according to Formula I

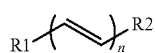

Formula I wherein n is 3 or more, preferably n is 3, 4 or 5, more preferably n is 3; and R1 and R2 are independently selected from aryl or heteroaryl, preferably aryl, more preferably phenyl. Preferably, the reporter dye is 1,6-diphenyl-1,3,5-hexatriene. Reporter dyes such as these are long, thin and hydrophobic, which means they are well suited to binding within a protein barrel lumen. Moreover, reporter dyes such as these do not provide an optical signal in free solution. However, on binding to a protein barrel lumen, the unconjugated chain twists and can provide a fluorescent signal in response to ultraviolet light.

The sensor array can comprise at least 10 sensors, preferably at least 50 sensors, more preferably at least 100 sensors, yet more preferably at least 300 sensors, wherein the protein barrel is different in each of the at least 10, 50, 100 or 300 sensors respectively. It is predicted that about 16 sensors, each with a different protein barrel, would be required to detect most commercially relevant small and macromolecular analytes. Of course, flatbed plate readers are typically set up to read 96-, 384- and 1536-well plates, although controls and replicates will usually bring down the number of unique sensors in any plate.

The sensor array can comprise at least one further sensor, wherein the reporter dye is different in the at least one further sensor. Varying the reporter dye is another way to achieve a variation in signal across the array. By using a reporter dye with different physicochemical properties to those of Formula I, the ability to distinguish different analytes is further improved. Typical reporter dyes that can be used include all napthalene dyes, such as 6-propionyl-2-dimethylaminonaphthalene (prodan).

According to a second aspect, the invention provides a microarray chip comprising a sensor array according to the first aspect of the invention. As mentioned above, it is possible to fabricate a microarray chip using the protein barrel and reporter dye. This can be a low cost, disposable or reusable microarray with a powerful ability to identify a broad range of analytes. The microarray can be read by a smartphone, making this sensor technology available for use by the population at large.

According to a third aspect, the invention provides for the use of a protein barrel and reporter dye for sensing an analyte, wherein the protein barrel defines a lumen; and the reporter dye is bound to the lumen reversibly. The protein barrel may have any of the features of the protein barrel according to the first aspect of the invention. The reporter dye may have any of the features of the reporter dye according to the first aspect of the invention.

According to a fourth aspect, the invention provides a method of using a sensor array according to the first aspect of the invention, the method comprising the steps of: (a) providing a sensor array according to the first aspect of the invention, (b) applying a composition for testing to the sensor array, (c) allowing the sensor array to develop, and (d) comparing the developed sensor array to a predetermined standard.

Step (d) can comprise the use of computational pattern recognition.

DESCRIPTION

Figure 1:
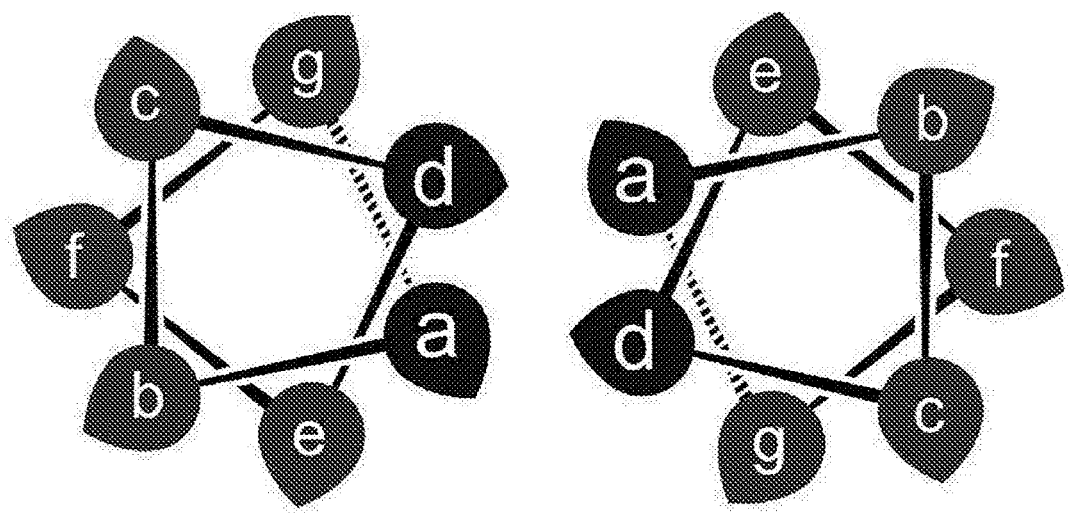
FIG. 1 is a schematic showing the abcdefg heptad repeat units of two alpha helices in a coiled-coil arrangement.

The first aspect of the invention provides a sensor array comprising at least two sensors. The sensor array can be provided, for example, in a multiwell plate. In this case, the different sensors would be in different wells.

The sensor array comprises at least two sensors. Two sensors is the minimum number of sensors needed to define an array. A larger number of sensors can be included in the array. For example, the array can comprise at least 10 sensors, preferably at least 50 sensors, more preferably at least 100 sensors, yet more preferably at least 300 sensors. The protein barrel is different in each of the at least two, 10, 50, 100 or 300 sensors respectively.

The requirement for the protein barrel to be different in structure in the claimed sensors does not preclude that the sensor array can contain yet further sensors that are merely replicate sensors, controls, or make use of the same protein barrel but with a different reporter dye. Indeed, the use of replicate sensors is a common strategy to improve data quality. In other words, the sensor array comprises a number of different sensors with different protein barrels, but there will usually be further sensors in the sensor array with the same protein barrels. These further sensors are usually replicates for data quality, controls, or sensors that use a different reporter dye. However, within the sensor array, there must at least be the claimed number of sensors wherein the protein barrel is different in structure.

Each sensor comprises a protein barrel. A protein barrel is a protein that defines a lumen. The protein barrel therefore has a lumen surface and an external surface. A lumen is a tubular cavity within the protein. The tubular cavity is typically elongated, i.e. long and narrow. Usually, the lumen would be open at both ends to allow for displacement of molecules within the lumen. However, in certain embodiments, the lumen may be blocked at one or at both ends to trap specific molecules within the lumen.

The protein barrel is different in structure in the different sensors. By this, we mean that there is at least one difference by which the protein barrels can be distinguished. This difference could include a point mutation in an amino acid, or an amino acid that has been derivatised or functionalised. This difference could also include a change in length or width of the protein barrel. This difference could also include a change in type of protein barrel.

Due to the possibility of making very different chemical environments by using a limited number of differences in the protein backbone, in certain embodiments of the invention, the different protein barrels may have similar protein backbones. For example, the different protein barrels may all be of the same type. In one embodiment, the different protein barrels may all be alpha helical barrels. In another embodiment, it may be that the different protein barrels are within 50% sequence identity, 70% sequence identity or 90% sequence identity.

A number of protein barrel types are known, including alpha helical barrels, beta barrels, ion channels, TIM barrels and other pore forming proteins.

Alpha helical barrels are protein barrels that comprise five or more alpha helices. The alpha helices arrange in a pattern where they are substantially aligned with each other, side-by-side, to form a tube-like shape. This is known as a coiled-coil fold (also known as coiled-coil structures or assemblies), and has been well characterised previously. Representative examples include Malashkevich et al., 1996; Koronakis et al., 2000; Zaccai et al., 2011; Fletcher et al., 2012; Meusch et al., 2014; Sun et al., 2014; Thomson et al., 2014; Collie et al., 2015; and Lombardo et al., 2016. Examples of coiled-coil folds comprising different alpha helix numbers can be seen in FIGS. 1-4.

Figure 4:
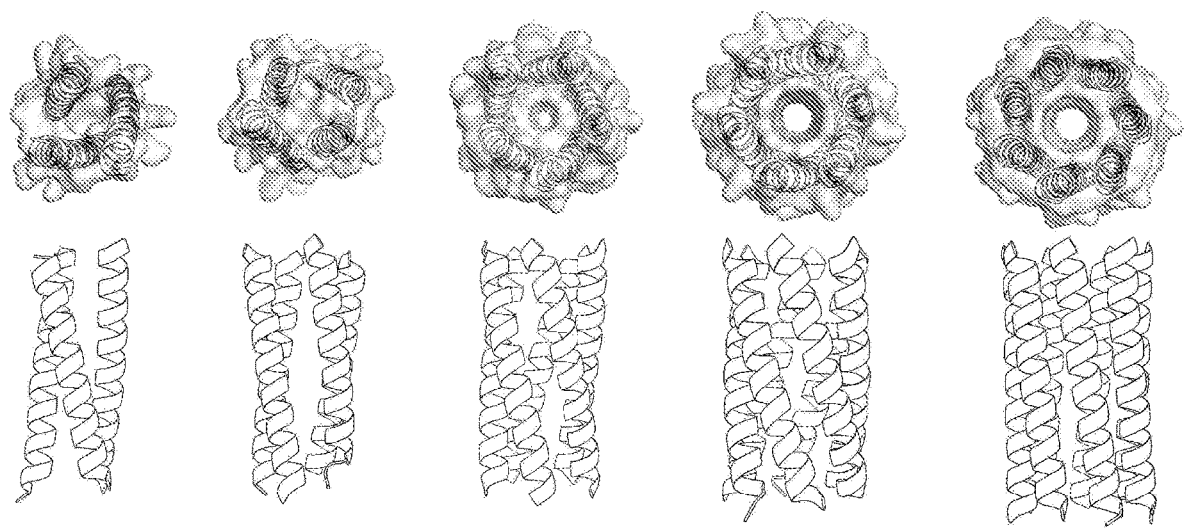
FIG. 4 shows top-down and side views of x-ray crystal structures of coiled-coil folds comprising 3, 4, 5, 6 and 7 alpha helices, corresponding to PDP IDs 4DZM, 4DZL, 3R4A, 4PN8, 4PN9 and 4PNA, respectively.

As can be seen in FIG. 4, coiled-coil folds can occur with 3 and 4 alpha helices. However, it is not until the number of alpha helices reaches 5 that a lumen forms. Coiled-coils with 5 or more alpha helices form a lumen, and therefore constitute alpha helical barrels.

Thomson 2014 reports that five alpha helical barrels have a lumen diameter of about 5.7 Å, six alpha helical barrels have a lumen diameter of about 6.0 Å or about 7.4 Å, and seven alpha helical barrels have a lumen diameter of about 7.6 Å, as measured by x-ray crystallography. In certain embodiments, the protein barrels have a lumen diameter of greater than about 5 Å, more preferably more than about 5.5 Å. In certain embodiments, the protein barrels have a lumen diameter of less than about 10 Å, more preferably less than about 8 Å.

Figure 2:
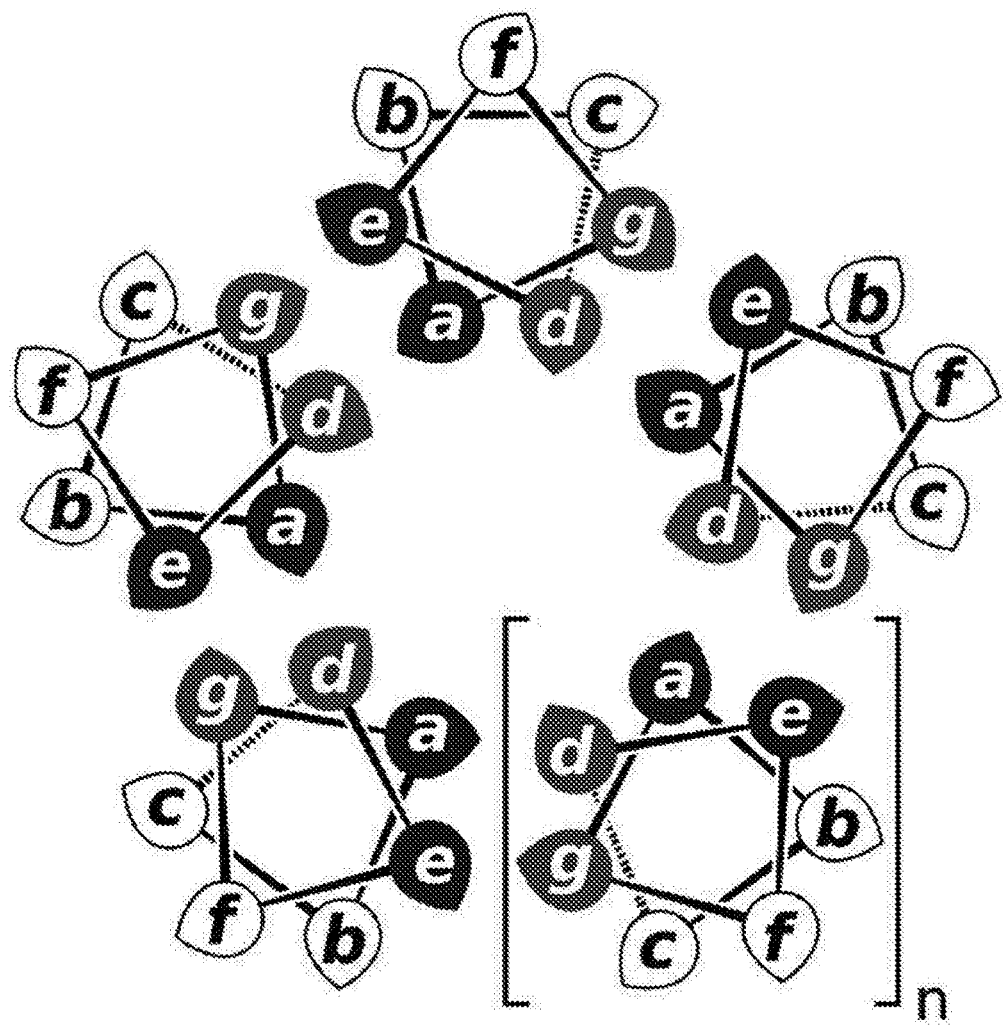
FIG. 2 is a schematic showing the abcdefg heptad repeat units of five or more alpha helices in a coiled-coil alpha helical barrel.
Figure 3:
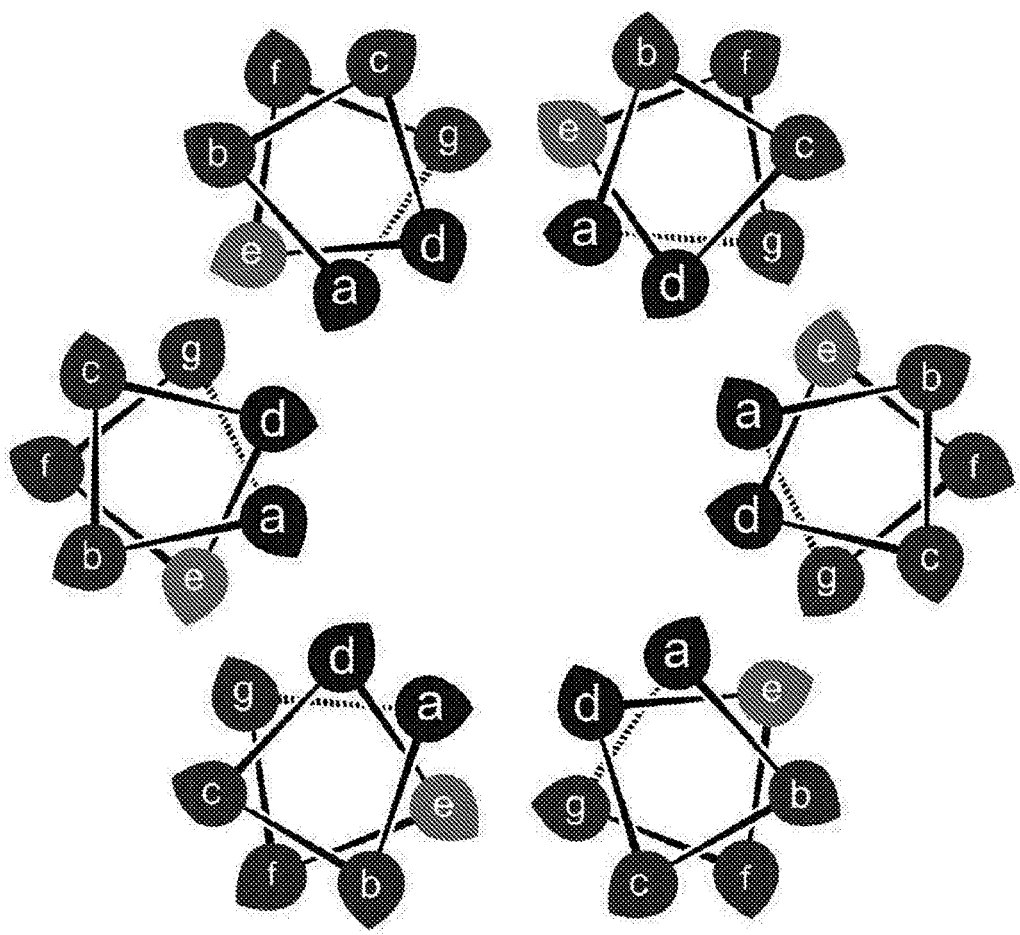
FIG. 3 is a schematic showing the abcdefg heptad repeat units of a six-helix barrel.

A common structural feature in coiled-coil folds, such as in alpha helical barrels, is that each alpha helix can independently comprise a sequence having a repeat unit with sequence abcdefg, wherein 50% or more of the a and d positions are hydrophobic amino acids and wherein 50% or more of the b, c, e, f and g positions are polar amino acids. In particular, having hydrophobic amino acids at the e and g positions can encourage alpha helix barrel formation, as can be seen in FIGS. 2 and 3. In one example, all the b, c and f positions can be polar amino acids, while all e and/or all g positions are hydrophobic amino acids.

In further embodiments, 60% or more, 75% or more, or 90% or more of the a and d positions are hydrophobic amino acids. In yet further embodiments, 60% or more, 75% or more, or 80% or more of the b, c, e, f and g positions are polar amino acids.

In particular examples, the repeat unit with sequence abcdefg can be selected from the list consisting of: In specific embodiments the repeat unit can be selected from the list consisting of: LQKIEfI (SEQ ID NO: 1), LKAIAfE (SEQ ID NO: 2), LKEIAfS (SEQ ID NO: 3), IKEIAfS (SEQ ID NO: 4), LKEIAfA (SEQ ID NO: 5), FKEIAfA (SEQ ID NO: 6), IKEIAfA (SEQ ID NO: 7), IKEVAfA (SEQ ID NO: 8), VKEVAfA (SEQ ID NO: 9), VKEIAfA (SEQ ID NO: 10), MKEIAfA (SEQ ID NO: 11), LKQIEfI (SEQ ID NO:

12), LKEVAfA (SEQ ID NO: 13), VKELAfA (SEQ ID NO: 14), IKELSfA (SEQ ID NO: 15), IKELAfS (SEQ ID NO: 16), LKELAfS (SEQ ID NO: 17), FKEIAfA (SEQ ID NO: 18) and LKELAfA (SEQ ID NO: 19); wherein f may vary between repeat units.

While these repeat units represent the basic building block of an alpha helix, there may of course be point mutations such that not every unit is an identical repeat. In any given alpha helix, or in the alpha helical barrel, up to 40%, preferably 25%, more preferably 10%, of the amino acid residues may deviate from the repeat unit. It can be seen from FIGS. 2 and 3 that position f is directed towards the bulk solvent and plays little role in assembly of the alpha helices with each other. The amino acid residue at position f is therefore less important, and can vary between repeat units. Position f is therefore usually a polar amino acid to assist with water solubility of the alpha helical barrel. However, position f is also a good candidate for further functionalisation.

Each alpha helix can comprise at least three repeat units. Examples of full length sequences based on the above repeat units include the following.

| Peptide Name | Sequence cdefgabcdefgabcdefgabcdefgab |
|---|---|
| CC-Pent | Ac-GKIEQILQKIEKILQKIEWILQKIEQILQG-NH$_2$ (SEQ ID NO: 20) |
| CC-Hex | Ac-GELKAIAQELKAIAKELKAIAWELKAIAQG-NH$_2$ (SEQ ID NO: 21) |
| CC-Hex2 | Ac-GEIAKSLKEIAKSLKEIAWSLKEIAKSLKG-NH$_2$ (SEQ ID NO: 22) |
| CC-Hept | Ac-GEIAQALREIAKALREIAWALREIAQALRG-NH$_2$ (SEQ ID NO: 23) |
| CC-Hex2-I10K | Ac-GEIAKSLKEKAKSLKEIAWSLKEIAKSLKG-NH$_2$ (SEQ ID NO: 24) |
| CC-Hept-I17K | Ac-GEIAQALREIAKALREKAWALREIAQALRG-NH$_2$ (SEQ ID NO: 25) |
| CC-Hept-I24D | Ac-GEIAKALREIAKALREIAWALREDAKALRG-NH$_2$ (SEQ ID NO: 26) |
| CC-Hept-I24K | Ac-GEIAQALREIAKALREIAWALREKAQALRG-NH$_2$ (SEQ ID NO: 27) |
| CC-Hept-I24E | Ac-GEIAKALREIAKALREIAWALREEAKALRG-NH$_2$ (SEQ ID NO: 28) |
| AIKEVA | Ac-GEVAQAIKEVAKAIKEVAWAIKEVAQAIKG-NH$_2$ (SEQ ID NO: 29) |
| AIKEIA | Ac-GEIAQAIKEIAKAIKEIAWAIKEIAQAIKG-NH$_2$ (SEQ ID NO: 30) |
| AVKEIA | Ac-GEIAQAVKEIAKAVKEIAWAVKEIAQAVKG-NH$_2$ (SEQ ID NO: 31) |
| AVKEVA | Ac-GEVAQAVKEVAKAVKEVAWAVKEVAQAVKG-NH$_2$ (SEQ ID NO: 32) |
| ALKEVA | Ac-GEVAQALKEVAKALKEVAWALKEVAQALKG-NH$_2$ (SEQ ID NO: 33) |
| AVKELA | Ac-GELAQAVKELAKAVKELAWAVKELAQAVKG-NH$_2$ (SEQ ID NO: 34) |
| SIKELA | Ac-GELAQSIKELAKSIKELAWSIKELAQSIKG-NH$_2$ (SEQ ID NO: 35) |
| AIKELS | Ac-GELSQAIKELSKAIKELSWAIKELSQAIKG-NH$_2$ (SEQ ID NO: 36) |
| SIKELA | Ac-GELAQSIKELAKSIKEEAWSIKELAQSIKG-NH$_2$ (SEQ ID NO: 37) |
| ALKELA | Ac-GELAQALKELAKALKELAWALKELAQALKG-NH$_2$ (SEQ ID NO: 38) |
| SLKELA | Ac-GELAQSLKELAKSLKELAWSLKELAQSLKG-NH$_2$ (SEQ ID NO: 39) |
| ALKELA | Ac-GELAQALKELAKALKEQAWALKELAQALKG-NH$_2$ (SEQ ID NO: 40) |
| ALKELA | Ac-GELAQALKELAKALKEEAWALKELAQALKG-NH$_2$ (SEQ ID NO: 41) |
| AFKEIA | Ac-GEIAQAFKEIAKAFKEIAWAFKEIAQAFKG-NH$_2$ (SEQ ID NO: 42) |
| AMKEIA | Ac-GEIAQAMKEIAKAMKEIAWAMKEIAQAMKG-NH$_2$ (SEQ ID NO: 43) |
| CCHept-I17C | Ac-GEIAQALKEIAKALKECAWALKEIAQALKG-NH$_2$ (SEQ ID NO: 44) |

Each alpha helix listed above is not covalently linked to any other alpha helices within the fully formed alpha helical barrel. Instead, the alpha helices self-assemble. The alpha helical barrels formed from the peptides listed above comprise identical alpha helices. However, in different embodiments, the alpha helices within an alpha helical barrel can be non-identical. With non-identical alpha helices that are not covalently linked, attention should be paid to the different permutations of alpha helical barrels that can self-assemble. Alternatively, the alpha helical barrel can comprise a single and continuous amino acid backbone. This affords a much greater level of control over the alpha helices that assemble to form the alpha helical barrel.

Beta barrels and ion channels are well-known natural protein barrel motifs that can be used in the present invention in a similar way to alpha helical barrels. TIM barrels can also be used. These are water soluble.

The protein barrel can comprise a non-natural amino acid. This may be an enantiomer of a natural amino acid, a natural amino acid that has been further functionalised, or any other amino acid. The rigid structure of protein barrels generally allows for substitution of a number of amino acids without compromising the fold of the protein barrel.

For example the table below shows how 3 non-proteinogenic peptides are incorporated into the array of 15 barrels and a DPH control by replacing 3 proteinogenic peptides.

| DPH control | CC-Pent (ILKQIE) | DPH control | CC-Pent (ILKQIE) |
|---|---|---|---|
| CC-Hept-I17C | CCHex (ELKAIA) | CC-Hept-I17C | CCHex (ELKAIA) |
| AFKEIA | CC-Hex2 (SLKEIA) | AFKEIA | CC-Hex2 (SLKEIA) |
| AIKEIA | CC-Hept (ALKEIA) | AKEIA | CC-Hept (ALKEIA) |
| AIKEVA | CC-Hept-I24D | AIKEVA | CC-Hept-I24D |

-continued

| | | | |
|---|---|---|---|
| AVKEVA | CC-Hept-I24E | AVKEVA | CC-Hex-L24Nle |
| AVKEIA | CC-Hept-I24K | AVKEIA | CC-Hept-I2SNle |
| AMKEIA | CC-Hept-I17K | AMKEIA | CC-Hept-dL (AdLKEIA) |
| Proteinogenic array | | Non-proteinogemc array | |

As can be seen, peptides in the standard proteinogenic array are shown on the left and the non-proteinogenic array on the right incorporates 3 peptide sequences (SEQ ID NOs: 46-48) with unnatural amino acids. Nle=Norleucine, dL=Dehydroleucine.

In one embodiment, the non-natural amino acid is an amino acids that has been modified by chemically linking a protein substrate. Such methods of chemical linkage are well known. The protein substrate would typically be linked to a residue on the external surface of the protein barrel. Where an alpha helical barrel is used, position f of the heptad repeat on an alpha helix would be a suitable candidate for the anchor for the linker. The protein substrate can comprise an enzyme substrate, receptor substrate and/or antibody substrate. By providing a protein substrate, the target protein can bind to the protein barrel and/or chemically modify the protein substrate. Either the binding of the protein or the chemical modification of the protein substrate can change the configuration of the protein barrel lumen and, in turn, disrupt binding of the reporter dye.

Each sensor of the sensor array comprises a reporter dye. A dye is a molecule that can provide an optical signal. The optical signal is typically in the ultraviolet and/or visible spectrum. By this, we mean a molecule that can provide a signal in the ultraviolet-visible region of the electromagnetic spectrum. The optical signal may be an absorption or luminescence signal. Preferably, the optical signal is fluorescence.

In the sensor array, the reporter dye is bound to the lumen reversibly. By this, we mean that the reporter dye is bound entirely, or substantially, within the protein barrel lumen.

The binding is reversible, meaning that the reporter dye is free to unbind from the lumen, or to undergo changes in binding within the lumen. This reversible binding is typically mediated by non-covalent interactions. A particularly preferable form of reversible binding is mediated by a hydrophobic reporter dye binding within a hydrophobic lumen. Labile covalent binding may also be used, for example, by means of an imine that can be readily cleaved by nucleophilic substitution.

To qualify as a reporter dye, the molecule should provide a different signal between being bound to the lumen and when this binding is disrupted. Disruption includes the reporter dye being ejected from the lumen or the reporter dye changing in configuration within the lumen. Ejection may occur when an analyte enters the lumen and displaces the reporter dye, in other words, by competitive binding. Ejection may also occur when an analyte binds to the exterior of a protein barrel such that the lumen changes in configuration to the extent that the reporter dye can no longer bind to the lumen. Alternatively, in this scenario, the change in configuration of the lumen results in a change in configuration of the reporter dye.

The reporter dye can be free to leave the lumen, for example, when the lumen is open at both ends. In an alternative embodiment, the reporter dye is encapsulated within the lumen. In this embodiment, the sensor relies on an analyte changing the lumen configuration such that the reporter molecule changes in configuration and exhibits a different signal.

In a preferred embodiment, the reporter dye provides an optical signal when bound to the lumen. For reporter dyes that can provide signals constituting a positive signal or no signal, depending on environment, (for example, a reporter dye that can fluoresce in one environment but cannot fluoresce in a different environment), the positive signal exists when the reporter dye is bound to the lumen. This is in contrast to a reporter dye where the optical signal exists in free solution, but does not exist when bound to the protein lumen.

The reporter dye can be a compound according to Formula I

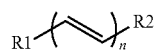

Formula I wherein n is 3 or more, preferably n is 3, 4 or 5, more preferably n is 3; and R1 and R2 are independently selected from aryl or heteroaryl, preferably aryl, more preferably phenyl. Reporter dyes in accordance with Formula I are therefore generally hydrophobic and able to adopt an elongate configuration. In a preferred embodiment, the dye is 1,6-diphenyl-1,3,5-hexatriene.

Alternative dyes may be used, including any naphthalene such as 6-propionyl-2-dimethylaminonaphthalene (prodan).

The sensor array may comprise at least one further sensor, wherein the reporter dye is different in the at least one further sensor. This allows for a sensor, or series of sensors, where a dye with very different properties is used. This can allow for more diversity to be brought to the sensor array.

The protein barrel may be immobilised on a substrate. The substrate may be, for example, a surface comprising a glass or plastics material. The protein barrel of any given sensor may be immobilised within the well of a multiwell plate. This would allow for washing and reuse of the protein barrel. The protein barrel of any given sensor may be immobilised on a flat surface, alongside neighbouring immobilised protein barrels from different sensors in the sensor array. This would allow for a single analyte to be readily applied across different sensors, without the protein barrels diffusing and interfering with each other. This would also allow for miniaturisation of the sensor array, allowing for a considerable number of sensors (i.e. perhaps at least 500 or at least 1000 sensors) to be present in a surface area of a small surface area (i.e. perhaps less than 5 or even less than 2 square centimetres). Such an array would provide a significant ability to distinguish between different analytes in a convenient and low-cost array. Such arrays are sometimes referred to as microchip arrays.

Techniques for immobilising protein barrels on a substrate are well-known (one example (Pai et al., 2012), discloses immobilisation of peptides in a microarray). Where the protein barrel comprises a number of self-assembled subunits, just one, multiple or all subunits may be individually immobilised. Typically, N- or C-terminal residues are used for immobilisation as this can lower the chance of disrupting the protein fold/3D structure. However, non-terminal residues may instead be used for linking the protein barrels to a substrate. For example, where an alpha protein barrel is used, an f position amino acid residue could provide a suitable anchor point for immobilisation. Often, a flexible linker can be used between the protein barrel and the substrate to allow a certain degree of movement of the immobilised protein barrel.

The reporter dye can also be immobilised. The reporter dye can be immobilised to the substrate, by means of a linker that allows the reporter dye enough freedom of movement to enter and leave the protein barrel lumen. Alternatively, the reporter dye can be immobilised by linking to the protein barrel. Again, a linker should be used that allows the reporter dye enough freedom of movement to enter and leave the protein barrel. A different possibility is that the reporter dye is encapsulated within the lumen. In this possibility, the ends of the lumen would be blocked after the reporter dye has bound to the lumen. Immobilisation of the dye and barrel further allows for a sensor array that is reusable or can be used in-line, without needing to consider that either the protein barrel or dye may wash away.

The protein barrel and reporter dye can be in a dry state. By this, we mean that the complex of protein barrel and reporter dye have been dried. Drying can be carried out by techniques including air drying and lyophilisation. In the dry state, the sensor array can be stored and transported easily. Prior to use, the sensor array should be rehydrated. Rehydration can be achieved by adding an aqueous solution in advance of applying a test sample, or by adding an aqueous test sample.

The analyte to be detected is usually a liquid or in solution. It would also be advantageous to be able to analyse gaseous analytes. As an alternative to immobilisation on a solid substrate, the protein barrel can be immobilised in or on a hydrogel or 3-dimensional porous scaffold substrate. This has the advantage that the sensor array could be used to detect gaseous analytes, as these can be dissolved in the hydrogel and hence accessible to the barrel. In particular, the barrels can be loaded into hydrogels, or 3-dimensional porous scaffolds, either covalently or non-covalently. Polymers (such as poly(ethylene glycol), polydimethyl siloxane and polyacrylamide), polysaccharides (such as chitosan, alginate and agarose) and peptide hydrogels are examples of materials that could be used to form the hydrogels.

The invention also provides for a microarray chip comprising a sensor array according to the first aspect of the invention. Microarray chip technology is well known. The microarray chip can be 3D printed. The microarray chip can comprise the sensor array in a dry state, wherein an aqueous test sample is soaked onto the chip. The microarray chip may be analysable by a smartphone.

The invention also provides for use of a protein barrel and reporter dye for sensing an analyte, wherein the protein barrel defines a lumen; and the reporter dye is bound to the lumen reversibly.

The invention also provides for a method of using a sensor array according to the first aspect of the invention, the method comprising the steps of: (a) providing a sensor array according to the first aspect of the invention, (b) applying a composition for testing to the sensor array, (c) allowing the sensor array to develop, and (d) comparing the developed sensor array to a predetermined standard.

The sensor arrays of the invention provide significant amounts of data. It can be very difficult or even impossible for the human eye to detect the differences that distinguish between analytes. However, these differences are much more amenable to computational approaches. As such, step (d) may comprise the use of computational pattern recognition. Examples of computational pattern recognition used in the art include principal component analysis (PCA), linear discriminant analysis (LDA), hierarchical cluster analysis (HCA) and artificial neural networks (ANN).

EXAMPLES

Example 1

Synthesis of Protein Barrels

Alpha helical barrels based on alpha helices with the following sequences (corresponding to the alpha helical barrels referred to in FIG. 6) were synthesised.

| Peptide | Number of helices in barrel | Sequence |
|---|---|---|
| CC-Hept-I17C | 7 | Ac-GEIAQALKEIAKALKECAWALKEIA QALKG-NH$_2$ |
| AFKEIA | 6 | Ac-GEIAQAFKEIAKAFKEIAWAFKEIA QAFKG-NH$_2$ |
| AIKEIA | 8 | Ac-GEIAQAIKEIAKAIKEIAWAIKEIA QAIKG-NH$_2$ |
| AIKEVA | 7 | Ac-GEVAQAIKEVAKAIKEVAWAIKEVA QAIKG-NH$_2$ |
| AVKEVA | 6 | Ac-GEVAQAVKEVAKAVKEVAWAVKEVA QAVKG-NH$_2$ |
| AVKEIA | 6 | Ac-GEIAQAVKEIAKAVKEIAWAVKEIA QAVKG-NH$_2$ |
| AMKEIA | 7 | Ac-GEIAQAMKEIAKAMKEIAWAMKEIA QAMKG-NH$_2$ |
| CC Pent (ILKQIE) | 5 | Ac-GKIEQILQKIEKILQKIEWILQKIE QILQG-NH$_2$ |
| CC-Hex (ELKAIA) | 6 | Ac-GELKAIAQELKAIAKELKAIAWELK AIAQG-NH$_2$ |
| CC-Hex2 (SLKEIA) | 6 | Ac-GEIAKSLKEIAKSLKEIAWSLKEIA KSLKG-NH$_2$ |
| CC-Hept (ALKEIA) | 7 | Ac-GEIAQALREIAKALREIAWALREIA QALRG-NH$_2$ |
| CC-Hept-I24D | 7 | Ac-GEIAKALREIAKALREIAWALREDA KALRG-NH$_2$ |
| CC-Hept-I24E | 7 | Ac-GEIAKALREIAKALREIAWALREEA KALRG-NH$_2$ |
| CC-Hept-I24K | 7 | Ac-GEIAQALREIAKALREIAWALREKA QALRG-NH$_2$ |
| CC-Hept-I17K | 7 | Ac-GEIAQALREIAKALREKAWALREIA QALRG-NH$_2$ |

The peptide sequences were synthesised and characterized using techniques previously described (Thomson et al., 2014).

Fmoc amino acids, DMF and Cl-HOBt were purchased from AGTC Bioproducts (Hessle, UK). Rink amide ChemMatrix solid support was purchased from PCAS BioMatris Inc (Saint-Jean-sur-Richelieu, Canada). TMA-DPH and farnesyl pyrophosphate (FPP) were purchased from Sigma-Aldrich (Gillingham, UK). Farnesol was purchased from Alfa Aesar (Heysham, UK). All other chemicals were purchased from Fisher-Scientific (Loughborough, UK). Unless stated otherwise, biophysical measurements were performed in HEPES buffered saline (HBS; 25 mM HEPES, 100 mM NaCl, pH 7.0). Peptide concentration was determined by UV-Vis on a ThermoScientific (Hemel Hemstead, UK) Nanodrop 2000 spectrometer ($\varepsilon_{280}$=5690 cm$^{-1}$).

Standard Fmoc solid-phase peptide synthesis was performed on a CEM (Buckingham, UK) Liberty Blue automated peptide synthesis apparatus with inline UV monitoring. Activation was achieved with DIC/Cl-HOBt. Fmoc deprotection was performed with 20% v/v morpholine/DMF. All peptides were produced as the C-terminal amide on Rink amide ChemMatrix solid support and N-terminally acetylated upon addition of acetic anhydride (0.25 mL) and pyridine (0.3 mL) in DMF (5 mL) for 30 minutes at room temperature (rt). Peptides were cleaved from the solid support by addition of trifluoroacetic acid (9.5 mL), triisopropylsilane (0.25 mL) and water (0.25 mL) for 3 hours with shaking at rt. The cleavage solution was reduced to approximately 5 mL under a flow of nitrogen. Crude peptide was precipitated upon addition of diethyl ether (40 mL) and recovered via centrifugation. The resulting precipitant was dissolved in 1:1 acetonitrile and water (≈15 mL) and lyophilised to yield crude peptide as a while solid.

Peptides were purified by reverse phase HPLC on a Phenomenex (Macclesfield, UK) Luna C18 stationary phase column (150×10 mm, 5 μM particle size, 100 Å pore size).

| Peptide | DPH $K_D$ (μM) | Prodan $K_D$ (μM) |
|---|---|---|
| CC-Pent | 22.4 ± 4.3 | — |
| CC-Hex | 7.1 ± 1.3 | — |
| CC-Hex2 | 9.5 ± 1.1 | 39.2 ± 6.8 |
| CC-Hept | 8.9 ± 2.2 | 40.5 ± 4.0 |

It can be seen from the table above that DPH binds to all four alpha helical barrels, while prodan did not bind to the alpha helical barrels comprising CC-Pent or CC-Hex. Prodan did not bind as tightly to these alpha helical barrels as DPH.

Example 3

Dye Displacement by Certain Analytes

After providing proof of concept that reporter dyes can bind within the lumen of alpha helical barrels, the next step was to demonstrate that bound reporter dyes can be displaced by analytes. The four analytes below were selected based on having hydrophobic properties and being able to adopt an elongate configuration, as these were postulated to have the best chance of displacing a reporter dye.

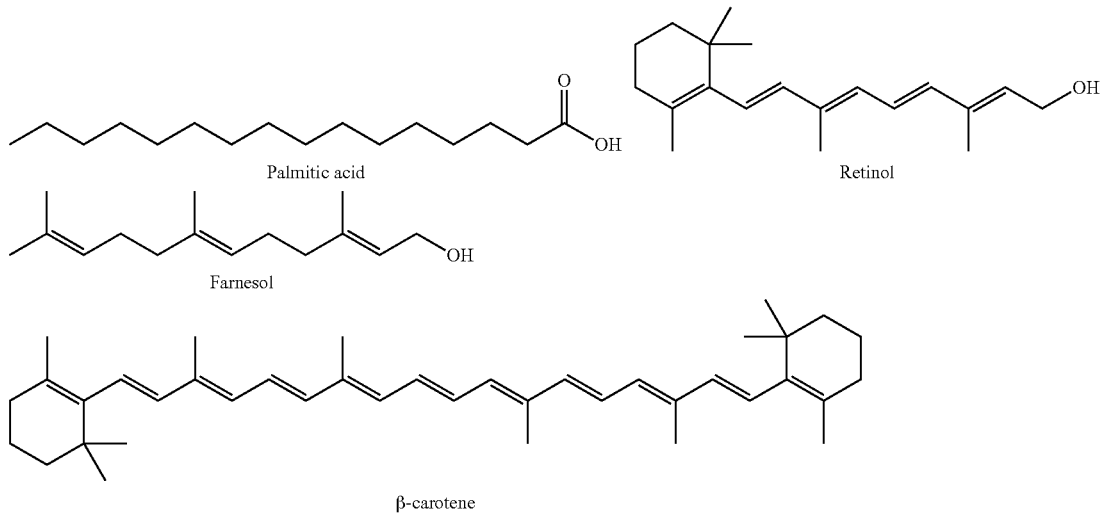

A 20-80% gradient of acetonitrile and water (with 0.1% TFA) was applied over 30 minutes. Fractions containing pure peptide were identified by analytical HPLC and MALDI-TOF MS, and were pooled and lyophilised.

Example 2

Binding of Dyes to Lumen

Initial experiments sought to demonstrate that reporter dyes would bind within the lumen of alpha helical barrels. The dyes 1,6-diphenyl-1,3,5-hexatriene (DPH) and 6-propionyl-2-dimethylaminonaphthalene (prodan) were assayed against a number of alpha helical barrels to determine their dissociation constants, $K_D$. DPH or prodan (1 μM) was incubated with varying concentrations of alpha helical barrel (0.5-500 μM) for up to 2 hours, and the fluorescent signal measured at the corresponding emission wavelength.

DPH was used as the reporter dye, and displacement of DPH was recorded using a standard competitive inhibition assay. In other words, the ability of an analyte to inhibit DPH binding was recorded by the inhibition constant $K_i$. Alpha helical barrels were incubated with DPH, or its cationic variant 1-(4-trimethylammoniumphenyl)-6-phenyl-1,3,5-hexatrienep-toluenesulfonate (TMA-DPH). Analyte was added (0.05-300 μM) and the fluorescence signal measured.

| Peptide | Palmitic acid $K_I$ (μM) | Retinol $K_I$ (μM) | Farnesol $K_I$ (μM) | B-carotene $K_I$ (μM) |
|---|---|---|---|---|
| CC-Pent | 1.1 ± 0.5 | 14.8 ± 4.1 | — | — |
| CC-Hex | 1.0 ± 0.3 | 6.4 ± 3.2 | 23.9 ± 2.4 | — |
| CC-Hex2 | 1.1 ± 0.3 | 4.6 ± 1.9 | 8.6 ± 1.3 | — |
| CC-Hept | 0.9 ± 0.3 | 4.0 ± 0.7 | 0.6 ± 0.2 | 12.1 ± 5.4 |

In all cases where competitive binding was observed, the inhibition constant was in the low micromolar range, similar to the dissociation constant of DPH indicating a similar strength of binding, and demonstrating that reporter dyes can be displaced by analytes.

Figure 5A:
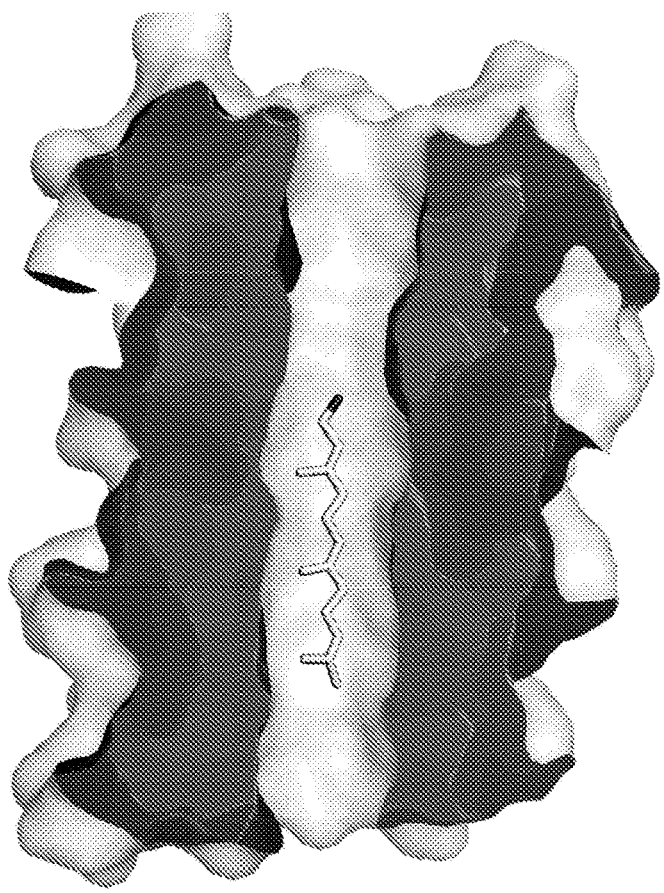
FIG. 5A shows a partial cutaway view of an x-ray crystal structure of an alpha helical barrel comprising CC-Hex2 with farnesol bound in the alpha helical barrel lumen.
Figure 5B:
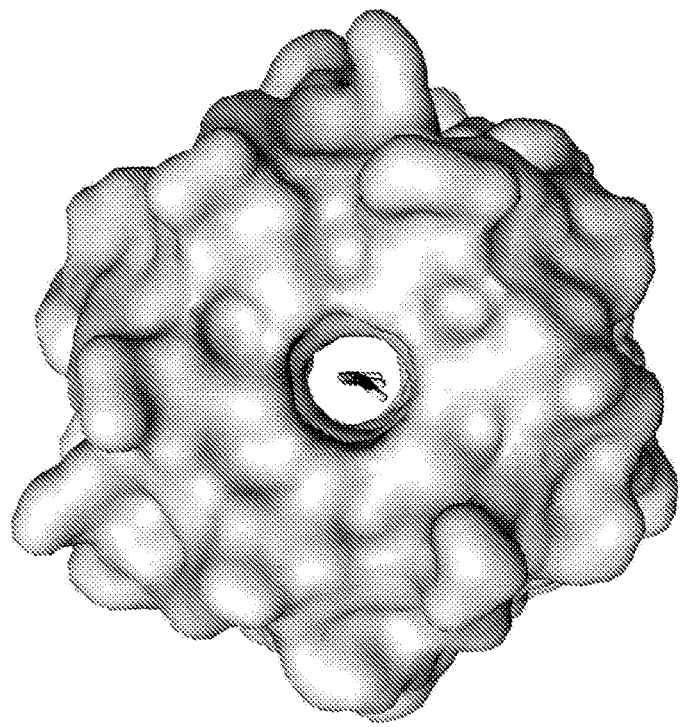
FIG. 5B shows a top down view of the x-ray crystal structure of FIG. 5A.

Further evidence of analyte binding was provided by an x-ray crystal structure of farnesol bound within the lumen of the CC-Hex2 alpha helical barrel. This is shown in FIGS. 5A and 5B. To obtain this crystal structure, a lyophilized sample of CC-Hex2 was resuspended in deionized water to a concentration of 5 mg ml$^{-1}$. Vapor-diffusion crystallization trials were set up at 19° C. using previously optimized conditions[1] (0.1 M Na HEPES, 4.3 M sodium chloride at pH 7.5) by mixing 1 μl of CC-Hex2 with 1 μl of reservoir solution. Diffraction-quality crystals were obtained in 4 days. A solution of farnesol (2 mM) was prepared in 40% v/v DMSO:$H_2O$ and crystals were soaked for 1, 5, 20, 60 and 120 min. At each time point, the crystals were soaked in the reservoir solution containing 20% glycerol before freezing.

X-ray diffraction data were collected at the Diamond Light Source (Didcot, UK) on beamline 104-1 at a wavelength of 0.98 Å. Data were processed with MOSFLM (Battye et al., 2011) and AIMLESS (Evans and Murshudov, 2013), as implemented in the CCP4 suite (Winn et al., 2011). Due to high anisotropy in the diffraction data, the resultant mtz file was truncated to 2 Å in the b-axis using the Diffraction Anisotropy Server (Strong et al., 2006).

The crystal structure was solved by molecular replacement using a poly-alanine model of CC-Hex2 (PDB 4pn8). The structure was obtained after iterative rounds of model building with COOT (Emsley and Cowtan, 2004) and refinement with PHENIX refine (Afonine et al., 2012). Refinement was carried out with torsion-libration-screw (TLS) (Zucker, Champ and Merritt, 2010) and non-crystallographic symmetry (NCS) parameters. An Omit map was calculated from the final model after removal of the ligand and refinement in Phenix. Ligand structures and geometric restraints were calculated using Phenix eLBOW (Moriarty, Grosse-Kunstleve and Adams, 2009).

The final refined structure showed good stereochemistry, as analysed by MOLPROBITY (Chen et al., 2010) and Ramachandran plots indicated that no residues fell outside preferred regions of backbone conformational space.

Example 4

Differential Arrays

Figure 6:
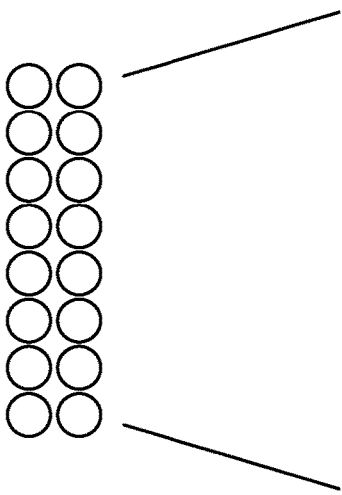
FIG. 6 shows a sensor array of different alpha helical barrels.

In a proof-of-principle experiment, 15 different alpha helical barrel designs, as set out in FIG. 6, were arrayed in 96-well plates. The different alpha helical barrels have a variety of sizes, with between 5 and 7 alpha helices. The different alpha helical barrels have different charges, with some being neutral, some having negatively charged carboxylate groups in the lumen and some having positively charged ammonium groups in the lumen.

Figure 7:
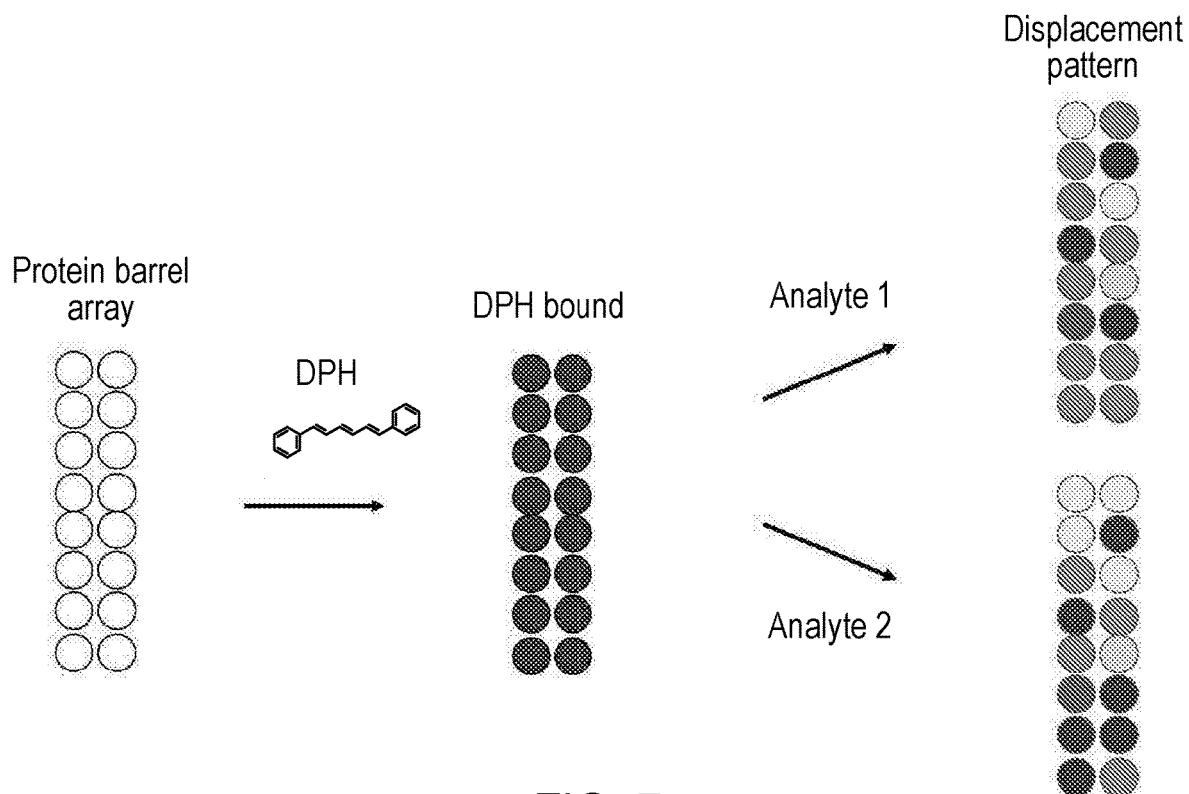
FIG. 7 is a schematic view showing how a sensor array is run, wherein protein barrels are added to the array, DPH reporter dye is bound and different analytes produce different displacement patterns or fingerprints.
Figure 8:
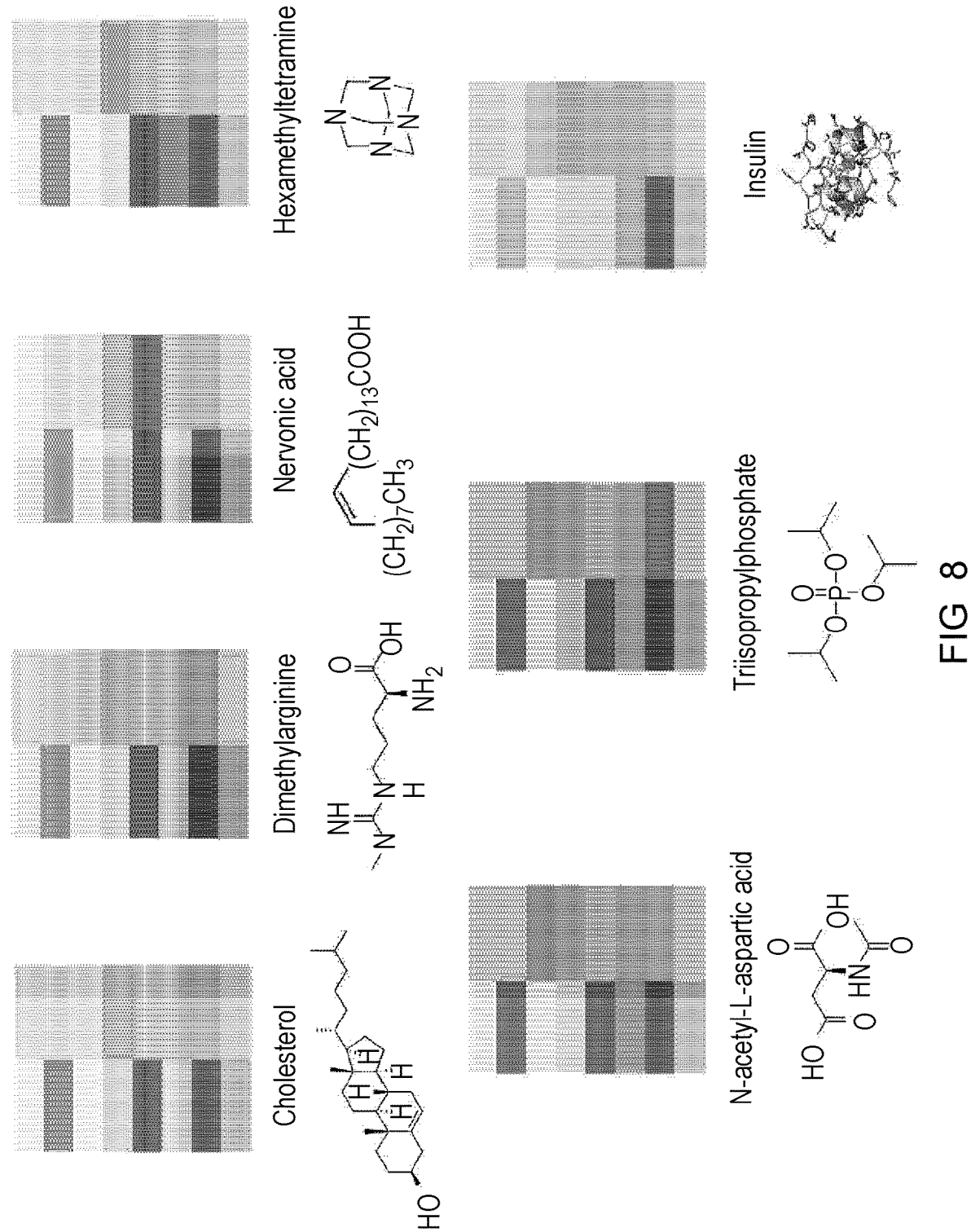
FIG. 8 shows displacement patterns for seven different analytes against the alpha helical barrel array described in FIG. 6.

The reporter dye DPH was added to each well and allowed to bind within the lumens of each alpha helical barrel. Seven different small and large molecules were then subjected to the sensor assay. The molecules and the optical signal of each sensor in each sensor assay is shown in FIG. 7. This Figure shows a unique binding signature for each of the molecules.

It is important to realise the significance of the molecules screened. Cholesterol and nervonic acid are largely hydrophobic molecules that might be expected to bind readily within the lumen of an alpha helical barrel. Furthermore, both can act as biomarkers, cholesterol for cardiovascular disease and nervonic acid for psychoses.

Dimethylarginine and N-acetyl-L-aspartic acid are highly polar amino acids, bearing multiple charges. It might be expected that these molecules would have little effect on an alpha helical barrel with an uncharged and hydrophobic lumen, however, a displacement pattern is seen even across such alpha helical barrels.

Hexamethyltetramine is an explosives precursor and again produces a distinct displacement pattern. Triisopropylphosphate is a sterically bulky nerve agent analogue.

A significant result was the sensor array pattern produced by insulin. Insulin is a peptide that should not be able to fit within the lumen of the alpha helical barrels used in the assay. However, a unique reporter dye displacement pattern was still produced. This provides evidence that even when analytes interact with the outer surface of an alpha helical barrel, reporter dye displacement can occur.

Figure 9:
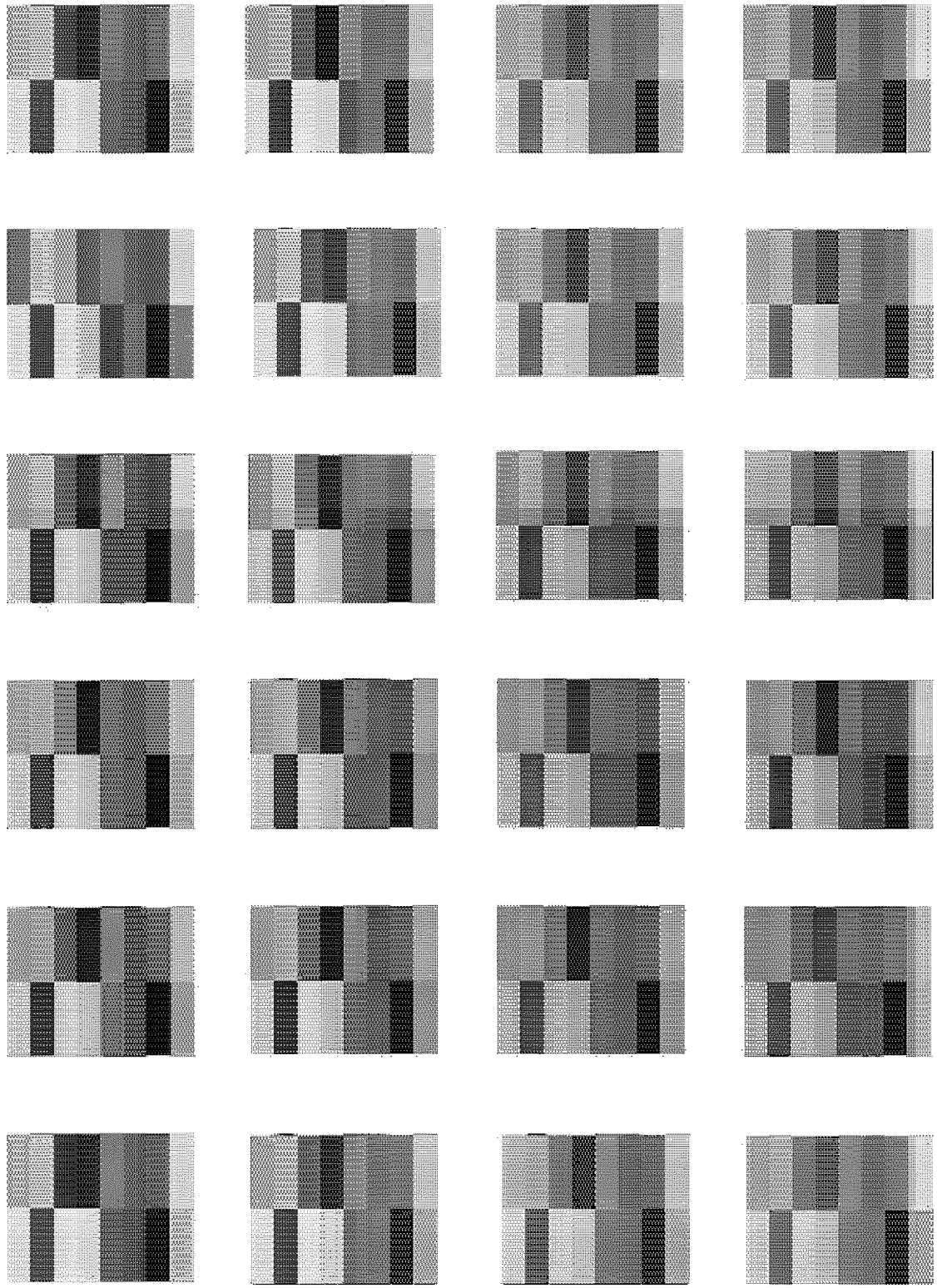
FIG. 9 shows replicate displacement patterns for cholesterol.

High reproducibility was observed in repeat assays, as can be seen for the replicate data presented in FIG. 9.

Figure 10:
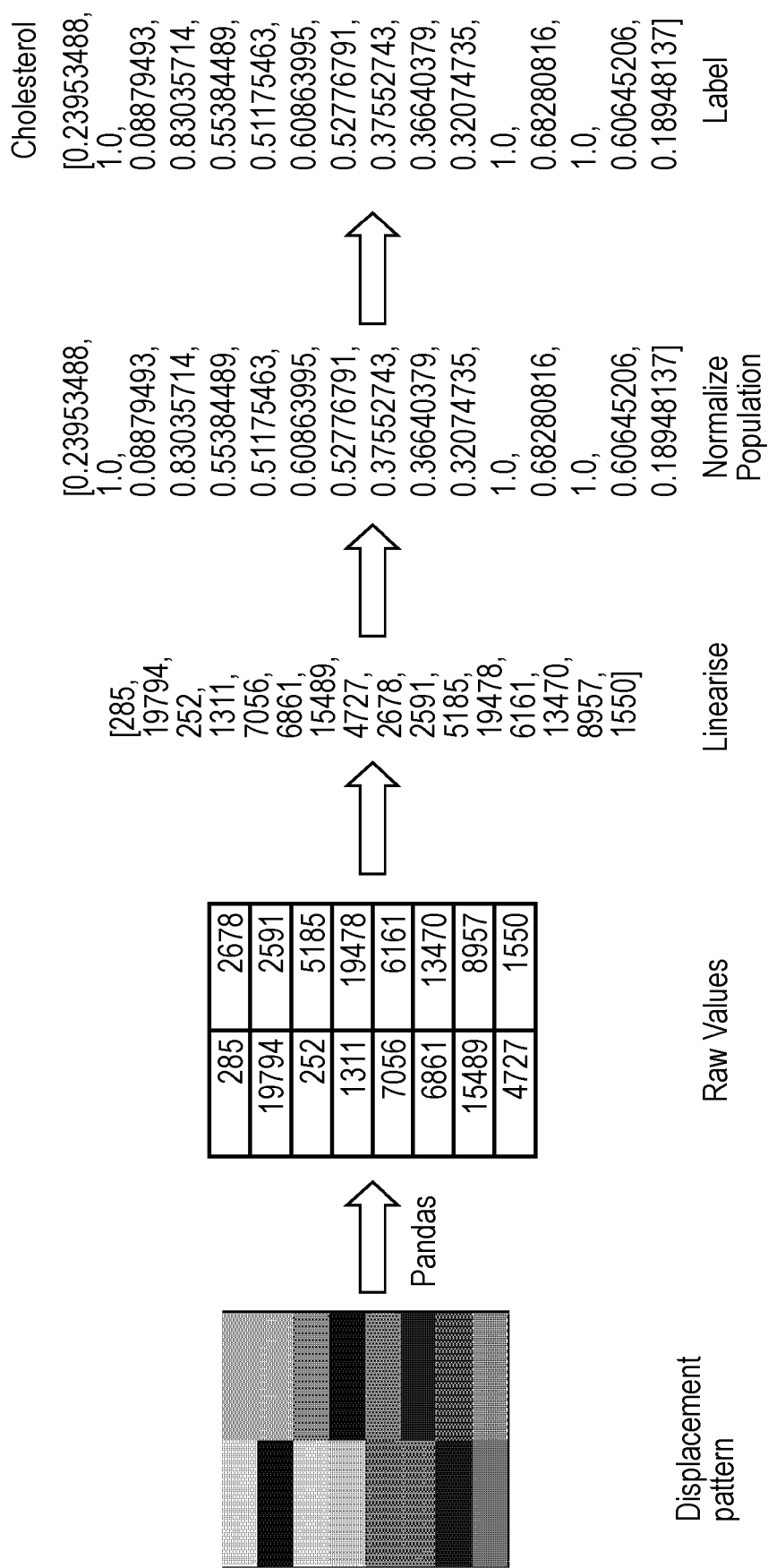
FIG. 10 shows a process for analysing a displacement pattern using computational methods.

FIG. 10 shows a workflow for applying computational pattern recognition to the sensor array results. The raw data is normalised, before looking for patterns that uniquely identify the analyte. By applying machine learning to the sensor array patterns for each molecule, the predictive power showed greater than 95% correct predictions.

Figure 11:
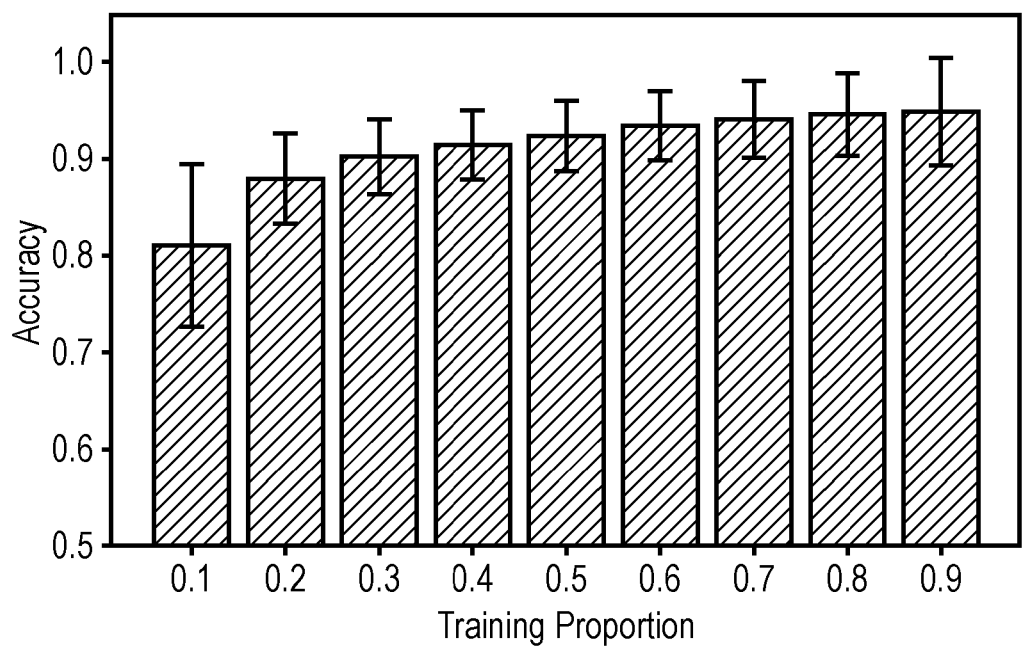
FIG. 11 is a chart showing how computational pattern recognition improves with training.

FIG. 11 shows how the prediction of analytes from naïve (unseen) data improves as the proportion of the data from known training sets is increased. In this case, by using random selection of just ≈30% of the 150 datasets of array signatures recorded for each of the known compounds, >90% of the predictions from the non-training-sets data are correct.

Example 5

Analysing Complex Mixtures

A selection of teas was analysed as a test bed for the analysis of complex mixtures. A total of 9 different boxes of tea bags where purchased from local supermarkets. This comprised three black teas (PG Tips, Yorkshire Tea, and Pukka English Breakfast), three Earl Grey Teas (Twinings The Earl Grey, Pukka Gorgeous Earl Grey, and Clipper Organic Earl Grey), and three Green Teas (Clipper Organic Green Tea, Twinings Pure Green Tea, and Tetley Pure Green Tea).

Teas were brewed in the laboratory as follows: Firstly, when applicable, strings and labels were removed from tea bags. Next, deionised water was boiled in a newly purchased kettle free of limescale. A single tea bag was placed in a 500 mL Schott bottle with a 50 mm stirrer bar before 250 mL of deionised water was added, and the tea allowed to brew for 5 min with stirring (100 rpm). After this time, 1 mL of the tea solution was removed, and diluted 1:10 with deionised water and the solution snap frozen in liquid nitrogen and then stored at −80° C. Fresh tea samples were prepared for each experimental replicate using an identical protocol.

Figure 12:
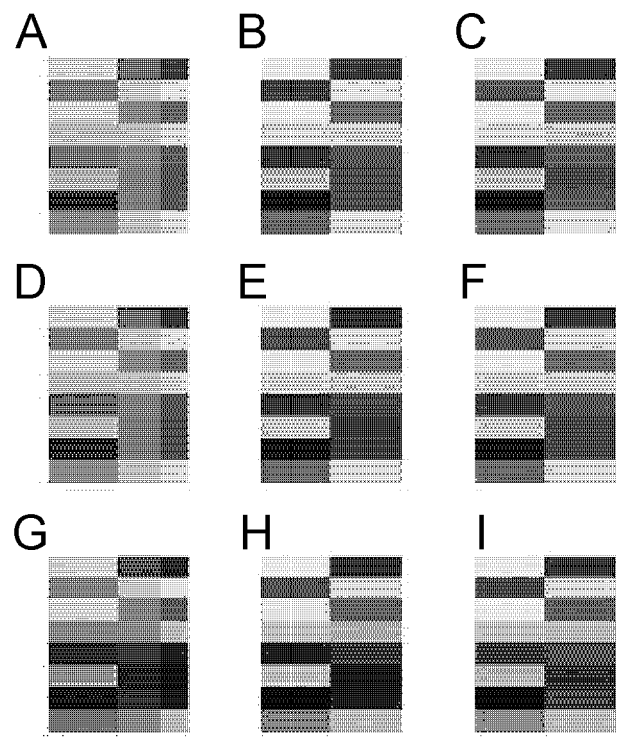
FIG. 12 shows the DPH displacement fingerprints produced by selected tea samples demonstrating that complex mixtures can be successfully analysed.

Using a suite of 15 barrel-forming peptide, plus a non-peptide containing control, tea was analysed by observing DPH displacement to yield fingerprints as depicted in FIG. 12. FIG. 12 shows the DPH displacement fingerprints produced by selected tea samples as follows: Panel A PGTIPS; Panel B Pukka English Breakfast; Panel C Yorkshire Tea; Panel D Clipper Organic Earl Grey; Panel E Pukka Gorgeous Earl Grey; Panel F Twinings The Earl Grey; Panel G Clipper Organic Green Tea; Panel H Tetley Pure Green Tea; and Panel I Twinings Pure Green Tea.

Implementing machine leaning techniques, tea could be successful classified by class (i.e. Black, Earl Grey or Green Tea) with 82.3% accuracy and by specific type with 90.0% accuracy.

Example 6

Analysing Epimers

Figure 13:
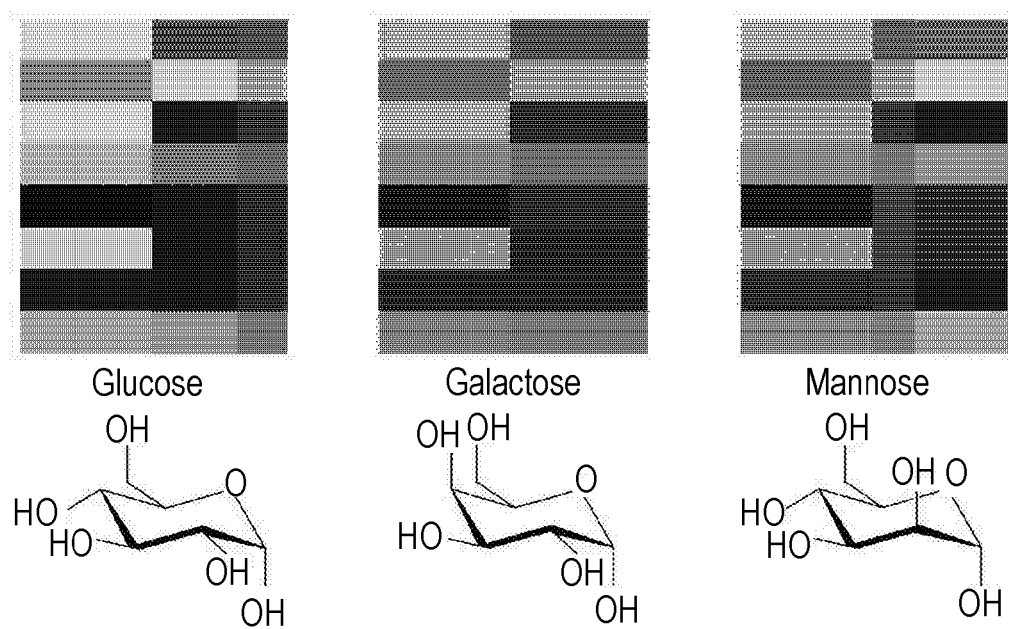
FIG. 13 shows across the top the DPH displacement fingerprints for glucose, galactose and mannose and across the bottom the structure of the epimers, and demonstrates that the invention can be used to distinguish epimers.

Glucose, galactose and mannose were analysed in an array of 15 peptides and a DPH control. These three sugars are epimers in that they differ by configuration and a single stereo-centre. Solutions of each of the three were prepared at 10 mM concentration ion water before being analysed at 1 mM final concentration in the barrel array in which DPH displacement was measured. Each sugar was examined using 24 replicates of each barrel, in each of two 384-well plates on two separate days (i.e. 4 plates for each sugar). The peptide array was able to distinguish between these 3 very similar molecules as shown by FIG. 13 which depicts the DPH displacement fingerprints for glucose, galactose and mannose across the top, and across the bottom the structure of each of the epimers.

Example 7

Non-natural Amino Acids

To demonstrate the use of non-natural amino acids, 3 non-proteinogenic peptides were incorporated into the array of 15 barrels and a DPH control by replacing 3 proteinogenic peptides.

| DPH control | CC-Pent (ILKQIE) | DPH control | CC-Pent (ILKQIE) |
|---|---|---|---|
| CC-Hept-I17C | CC-Hex (ELKAIA) | CC-Hept-I17C | CC-Hex (ELKAIA) |
| AFKEIA | CC-Hex2 (SLKEIA) | AFKEIA | CC-Hex2 (SLKEIA) |
| AIKEIA | CC-Hept (ALKEIA) | AIKEIA | CC-Hept (ALKEIA) |
| AIKEVA | CC-Hept-I24D | AIKEVA | CC-Hept-I24D |
| AVKEVA | CC-Hept-I24E | AVKEVA | CC-Hex-L24Nle |
| AVKEIA | CC-Hept-I24K | AVKEIA | CC-Hept-L28Nle |
| AMKEIA | CC-Hept-I17K | AVKEIA | CC-Hept-dL (AdLKEIA) |
| Proteinogenic array | | Non-proteinogenic array | |

As can be seen, peptides in the standard proteinogenic array are shown on the left and the non-proteinogenic array on the right incorporates 3 peptide sequences with unnatural amino acids. Nle=Norleucine, dL=Dehydroleucine.

Figure 14:
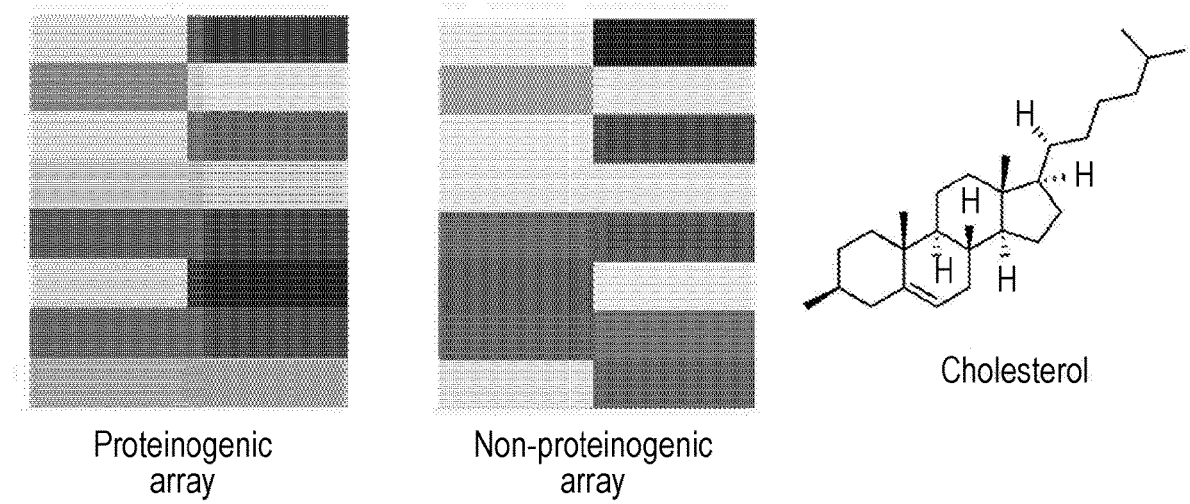
FIG. 14 is a comparison of DPH displacement fingerprints for cholesterol (right), at 1 µM final concentration, using proteinogenic (left) and non-proteinogenic (centre) peptide arrays.

Cholesterol was analysed at 1 µM and the DPH displacement fingerprints analysed. As can be seen in FIG. 14, a clear difference is observed when the proteinogenic (on the left) and non-proteinogenic (on the right) fingerprints are compared.

Example 8

D Amino Acid Peptides

To demonstrate the use of D-amino acids in the barrel array, an analogue of peptide ALKEVA comprising entirely D-Amino acids was prepared (i.e. peptide d-(AVKEVA), below)

d-(AVKEVA):
(SEQ ID NO: 45)
Ac-GevaqavkevakavkevawaykevaqakvG-NH$_2$

Figure 15:
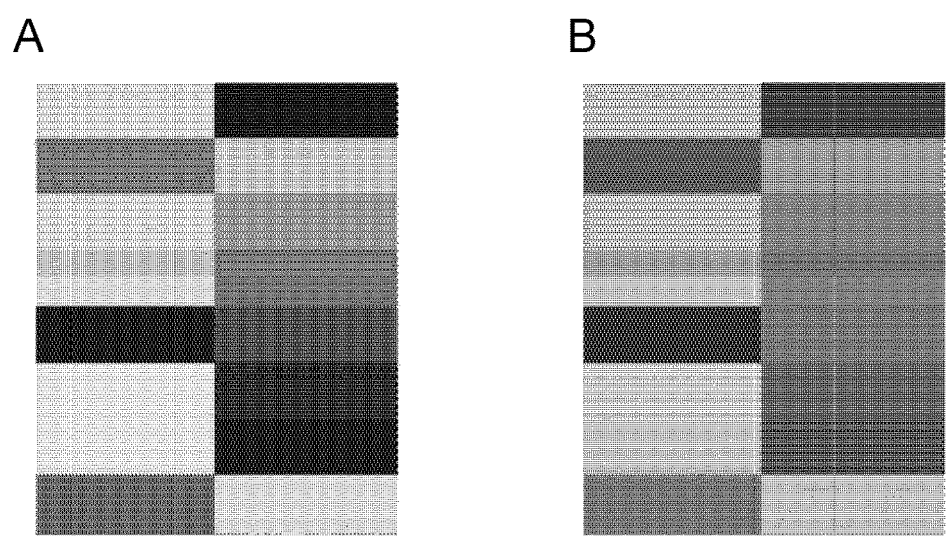
FIG. 15 shows DPH displacement fingerprints for N-Acetyl-L-aspartic acid (Panel A) and NG,NG-Dimethyl-arginine (Panel B) using a peptide barrel array including one all D-amino acid peptide (d-(avkeva)) which is represented by the block depicted on the left, second from bottom in each fingerprint.

This peptide, which possesses the opposite chirality to peptide ALKEVA at each chiral centre, was substituted into a 15 peptide barrel array (as listed in Example 1) in place of peptide AVKEIA. Using this modified array, two small molecules were analysed for DPH displacement: N-Acetyl-L-aspartic acid and NG,NG-Dimethylarginine. Solutions of each molecule were prepared at 10 µM in water before being examined at 1 µM concentration with 24 replicates in each of three 384-well plates. FIG. 15 shows the DPH displacement signatures for each of these two molecules. In particular FIG. 15 shows DPH displacement fingerprints for N-Acetyl-L-aspartic acid (Panel A) and NG,NG-Dimethylarginine (Panel B) using a peptide barrel array including one all D-amino acid peptide (d-(AVKEVA)) which is represented by the block depicted on the left, second from bottom in each fingerprint. From these data, machine learning techniques were implemented and the two molecules distinguished with 95.5% accuracy.

REFERENCES

Adams, M. M.; Anslyn, E. V. *Journal of the American Chemical Society* 2009, 131, 17068-17069

Afonine, P. V.; Grosse-Kunstleve, R. W.; Echols, N.; Headd, J. J.; Moriarty, N. W.; Mustyakimov, M.; Terwilliger, T. C.; Urzhumtsev, A.; Zwart, P. H.; Adams, P. D. *Acta Crystallographica Section D-Biological Crystallography* 2012, 68, 352.

Battye, T. G. G.; Kontogiannis, L.; Johnson, O.; Powell, H. R.; Leslie, A. G. W. *Acta Crystallographica Section D-Biological Crystallography* 2011, 67, 271.

Collie, G. W.; Pulka-Ziach, K.; Lombardo, C. M.; Fremaux, J.; Rosu, F.; Decossas, M.; Mauran, L.; Lambert, O.; Gabelica, V.; Mackereth, C. D.; Guichard, G. *Nature Chemistry* 2015, 7, 871-878.

Chen, V. B.; Arendall, W. B.; Headd, J. J.; Keedy, D. A.; Immormino, R. M.; Kapral, G. J.; Murray, L. W.; Richardson, J. S.; Richardson, D. C. *Acta Crystallographica Section D-Biological Crystallography* 2010, 66, 12.

Diehl, K. L.; Ivy, M. A.; Rabidoux, S.; Petry, S. M.; Müller, G.; Anslyn, E. V. *Proceedings of the National Academy of Sciences of the USA* 2015, 112, E3977-E3986.

Emsley, P.; Cowtan, K. *Act. Cryst D* 2004, 60, 2126.

Evans, P. R.; Murshudov, G. N. *Acta Crystallographica Section D-Biological Crystallography* 2013, 69, 1204.

Fletcher, J. M. et al. *ACS Synthetic Biology* 2012, 1, 240-250.

Ghanem, E.; Afsah, S.; Fallah, P. N.; Lawrence, A.; LeBovidge, E.; Raghunathan, S.; Rago, D.; Ramirez, M. A.; Telles, M.; Winkler, M.; Schumm, B.; Makhnejia, K.; Portillo, D.; Vidal, R. C.; Hall, A.; Yeh, D.; Judkins, H.; Ataide da Silva, A.; Franco, D. W.; Anslyn, E. V. *ACS Sensors* 2017, 2, 641-647.

Ivy, M. A.; Gallagher, L. T.; Ellington, A. D.; Anslyn, E. V. *Chemical Science* 2012, 3, 1717-2176.

Koronakis, V.; Sharif, A.; Koronakis, E.; Luisi, B.; Hughes, C. *Nature* 2000, 405, 914-919.

Kubarych, C. J.; Adams, M. M.; Anslyn E. V. *Organic Letters* 2010, 12, 4780-4783.

Lombardo, C. M.; Collie, G. W.; Pulka-Ziach, K.; Rosu, F.; Gabelica, V.; Mackereth, C. D.; Guichard, G. *Journal of the American Chemical Society* 2016, 138, 10522-10530.

Malashkevich, V. N.; Kammerer, R. A.; Efimov, V. P.; Schulthess, T.; Engel, J. *Science* 1996, 274, 761-765.

Meusch, D. et al. *Nature* 2014, 508, 61-65.

Moriarty, N. W.; Grosse-Kunstleve, R. W.; Adams, P. D. *Acta Crystallographica Section D-Biological Crystallography* 2009, 65, 1074.

Pai, J.; Yoon, T.; Kim, N. D.; Lee, I. S.; Yu, J.; Shin, I. *Journal of the American Chemical Society* 2012, 134, 19287-19296.

Strong, M.; Sawaya, M. R.; Wang, S. S.; Phillips, M.; Cascio, D.; Eisenberg, D. *Proceedings of the National Academy of Sciences of the United States of America* 2006, 103, 8060.

Sun, L. et al. *Nature* 2014, 505, 432-435.

Thomson, A. R.; Wood, C. W.; Burton, A. J.; Bartlett, G. J.; Sessions, R. B.; Brady, R. L.; Woolfson, D. N. *Science* 2014, 346, 485-488.

Umali, A. P.; Anslyn, E. V. *Curr. Op. Chem. Biol* 2010, 14, 685-692.

Umali, A. P.; Ghanem, E.; Hopfer, H.; Hussain, A.; Kao, Y.; Zabanal, L. G.; Wilkins, B. J.; Hobza, C.; Quach, D. K.; Fredell, M.; Heymann, H.; Anslyn, E. V. *Tetrahedron* 2015, 71, 3095-3099.

Winn, M. D.; Ballard, C. C.; Cowtan, K. D.; Dodson, E. J.; Emsley, P.; Evans, P. R.; Keegan, R. M.; Krissinel, E. B.; Leslie, A. G. W.; McCoy, A.; McNicholas, S. J.; Murshudov, G. N.; Pannu, N. S.; Potterton, E. A.; Powell, H. R.; Read, R. J.; Vagin, A.; Wilson, K. S. *Acta Crystallographica Section D-Biological Crystallography* 2011, 67, 235.

You, L.; Zha, D.; Anslyn, E. V. *Chemical Reviews* 2015, 115, 7840-7892.

Zaccai, N. R.; Chi, B.; Thomson, A. R.; Boyle, A. L.; Bartlett, G. J.; Bruning, M.; Linden, N.; Sessions, R. B.; Booth, P. J.; Brady, R. L.; Woolfson, D. N. *Nature Chemical Biology* 2011, 7, 935-941.

Zucker, F.; Champ, P. C.; Merritt, E. A. *Acta Crystallographica Section D-Biological Crystallography* 2010, 66, 889.

The invention claimed is:

1. A sensor array comprising at least two sensors, wherein each sensor comprises a protein barrel and a reporter dye;
   wherein the protein barrel defines a lumen; the reporter dye is bound to the lumen reversibly; and
   wherein the protein barrel is different in structure in the at least two sensors and further wherein the protein barrel comprises five or more alpha helices arranged as an alpha helical barrel.

2. A sensor array according to claim 1, wherein each alpha helix independently comprises a sequence having a repeat unit with sequence abcdefg, wherein 50% or more of the a and d positions are hydrophobic amino acids and wherein 50% or more of the b, c, e, f and g positions are polar amino acids.

3. A sensor array according to claim 2, wherein the repeat unit with sequence abcdefg is selected from the list consisting of: LQKIEfI (SEQ ID NO: 1), LKAIAfE (SEQ ID NO: 2), LKEIAfS (SEQ ID NO: 3), IKEIAfS (SEQ ID NO: 4), LKEIAfA (SEQ ID NO: 5), FKEIAfA (SEQ ID NO: 6), IKEIAfA (SEQ ID NO: 7), IKEVAfA (SEQ ID NO: 8), VKEVAfA (SEQ ID NO: 9), VKEIAfA (SEQ ID NO: 10), MKEIAfA (SEQ ID NO: 11), LKQIEfI (SEQ ID NO: 12), LKEVAfA (SEQ ID NO: 13), VKELAfA (SEQ ID NO: 14), IKELSfA (SEQ ID NO: 15), IKELAfS (SEQ ID NO: 16), LKELAfS (SEQ ID NO: 17), FKEIAfA (SEQ ID NO: 18), and LKELAfA (SEQ ID NO: 19); wherein f may vary between repeat units.

4. A sensor array according to claim 1, wherein each alpha helix comprises at least three repeat units.

5. A sensor array according to claim 1, wherein the protein barrel comprises a non-natural amino acid.

6. A sensor array according to claim 5, wherein the non-natural amino acid is an amino acid that has been modified by chemically linking a protein substrate.

7. A sensor array according to claim 6, wherein the protein substrate comprises an enzyme substrate, receptor substrate and/or antibody substrate.

8. A sensor array according to claim 1, wherein the protein barrel comprises a single and continuous amino acid backbone.

9. A sensor array according to claim 1, wherein the protein barrel is immobilised on a substrate which is a solid substrate or is a hydrogel.

10. A sensor array according to claim 1, wherein the protein barrel and reporter dye are in a dry state.

11. A sensor array according to claim 1, wherein the reporter dye provides an optical signal when bound to the lumen.

12. A sensor array according to claim 1, wherein the reporter dye is a compound according to Formula I

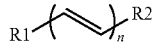

wherein n is 3, 4 or 5; and
R1 and R2 are independently selected from aryl or heteroaryl.

13. A sensor array according to claim 1, comprising at least 10 sensors, wherein the protein barrel is different in each of the at least 10 sensors.

14. A sensor array according to claim 13, comprising at least one further sensor, wherein the reporter dye is different in the at least one further sensor.

15. A microarray chip comprising a sensor array according to claim 1.

16. A method of sensing an analyte, comprising:
providing a sensor array comprising at least two sensors, wherein each sensor comprises a protein barrel and reporter dye for sensing the analyte, wherein the protein barrel defines a lumen and the reporter dye is bound to the lumen reversibly; and
further wherein the protein barrel is different in structure in the at least two sensors and the protein barrel comprises five or more alpha helices arranged as an alpha helical barrel.

17. A method of using a sensor array according to claim 1, the method comprising the steps of: (a) providing a sensor array according to claim 1, (b) applying a composition for testing to the sensor array, (c) allowing the sensor array to interact with the composition, and (d) comparing the developed sensor array to a predetermined standard.

18. A method according to claim 17, wherein step (d) comprises computational pattern recognition.

* * * * *